US010590405B2

(12) United States Patent
Covas et al.

(10) Patent No.: US 10,590,405 B2
(45) Date of Patent: Mar. 17, 2020

(54) METHOD FOR MODIFYING HUMAN CELL LINES TO PRODUCE FACTOR VII

(71) Applicant: FUNDAÇÃO HEMOCENTRO DE RIBEIRÃO PRETO—FUNDHERP, São Paulo (BR)

(72) Inventors: Dimas Tadeu Covas, São Paulo (BR); Marcela Cristina Corrêa de Freitas, São Paulo (BR); Virginia Picanço e Castro, São Paulo (BR); Kamilla Swiech, São Paulo (BR)

(73) Assignee: FUNDAÇÃO HEMOCENTRO DE RIBEIRÃO PRETO—FUNDHERP (BR)

( * ) Notice: Subject to any disclaimer, the term of this patent is extended or adjusted under 35 U.S.C. 154(b) by 0 days.

(21) Appl. No.: 15/577,212

(22) PCT Filed: Apr. 27, 2016

(86) PCT No.: PCT/BR2016/000041
§ 371 (c)(1),
(2) Date: Feb. 8, 2018

(87) PCT Pub. No.: WO2016/187683
PCT Pub. Date: Dec. 1, 2016

(65) Prior Publication Data
US 2018/0148705 A1  May 31, 2018

(30) Foreign Application Priority Data

May 27, 2015 (BR) .......................... 1020150123345

(51) Int. Cl.
*C12N 9/64* (2006.01)

(52) U.S. Cl.
CPC .... *C12N 9/6437* (2013.01); *C12Y 304/21021* (2013.01)

(58) Field of Classification Search
None
See application file for complete search history.

(56) References Cited

U.S. PATENT DOCUMENTS

| 4,784,950 A | 11/1988 | Hagen et al. ................. 435/68 |
| 6,114,146 A | 9/2000 | Herlitschka et al. ........ 435/69.7 |
| 6,265,183 B1 * | 7/2001 | Dorner ................. C07K 14/005 424/199.1 |
| 8,426,128 B2 * | 4/2013 | Stafford ............... C12N 9/0006 435/6.1 |
| 8,940,504 B2 | 1/2015 | Streenstrup et al. ......... 435/69.1 |
| 2004/0023333 A1 | 2/2004 | Hauser et al. .......... 435/69.6 |
| 2004/0185535 A1 | 9/2004 | Wilson et al. ............. 435/69.6 |
| 2009/0088370 A1 | 4/2009 | Winge ............................ 514/8 |
| 2010/0172891 A1 | 7/2010 | Fontes et al. ............... 424/94.5 |
| 2010/0331255 A1 | 12/2010 | Wallin ........................ 514/13.7 |
| 2012/0282687 A1 | 11/2012 | Koh et al. .................. 435/320.1 |
| 2014/0051122 A1 | 2/2014 | De Souza Russo Carbolante et al. ............................. 435/69.6 |
| 2017/0096684 A1 * | 4/2017 | Alton ................. A61K 48/0066 |

FOREIGN PATENT DOCUMENTS

| BR | PI0802690 | 3/2010 | ............. A61K 38/16 |
| BR | PI11053178 | 4/2013 | ............. C12N 5/071 |
| WO | WO0170763 | 9/2001 | ........... C07K 14/745 |
| WO | WO 2006/067116 | 6/2006 | ............... C12N 9/64 |
| WO | WO 2007/065173 | 6/2007 | ............. C12N 15/09 |
| WO | WO2013151666 | 10/2013 | ............. A61K 48/11 |

OTHER PUBLICATIONS

European Search Report issued in corresponding European Appln. No. 16798970.6-1111 dated Mar. 28, 2018 (11 pgs).
Spencer, H. Trent et al. "Lentiviral Vector Platform for Production of Bioengineered Recombinant Coagulation Factor VII" *Molecular Therapy* vol. 19, No. 2, 302-306 Feb. 2011 (8 pgs).
Da Rosa, N. G. et al. SK-HEP cells and lentiviral vector for production of human recombinant factor VIII. Biotechnol Lett. 2012. vol. 34, No. 8, pp. 1435-1443. doi: 10.1007/s 10529-012-0925-4. Abstract, first paragraph of section "Materiais e Metodos" (on p. 1436), first and last paragraphs of pp. 1437.
Freitas, M. C. C Clonagem e expressao do fator VII de coagulacao sanguinea em linhagens celulares humanas. 2015. Tese (Doutorado em Clinica Medica)—Faculdade de Medicina de Ribeirao Preto, Universidade de Sao Paulo, Ribeirao Preto, May 29, 2015. Disponible at: <http://www.teses.usp.br/teses/disponiveis/!7/17138ltde-05012016-091813/>. Acceso: 2016-06-1 4. Abstract, "Material e Metodos", figures 26 and 27.
Hansson, K & Stenflo, J. Post-translational modifications in proteins involved in blood coagulation. J Thromb Haemost. 2005. vol. 3, No. 12, pp. 2633-2648, 001:10.111 IIj.1 538-7836.2005.01 478.x. Figure 1 and Table 1.
International Preliminary Report on Patentability (w/translation) issued in application No. PCT/BR2016/000041, dated Nov. 28, 2017 (17 pgs).
International Search Report and Written Opinion (w/translation) issued in application No. PCT/BR2016/000041, dated Jul. 14, 2016 (27 pgs).
Mei et al., "Expression of human coagulation factor VIII in a human hybrid cell line, HKB11," Molecular Biotechnology, Oct. 2006, vol. 34, No. 2, pp. 165-178 (11 pgs).

(Continued)

*Primary Examiner* — Hope A Robinson
(74) *Attorney, Agent, or Firm* — Hayes Soloway P.C.

(57) ABSTRACT

A process for producing blood coagulation Factor VII in 3 human cell lines (HepG2, Sk-Hep, HKB-11) and to select the best recombinant protein producer is described. The murine line BHK-21 was used as control. The data allow to assert that the system used to modify cell lines was efficient, so that all the cells were satisfactorily modified, and produced the protein of interest of stable form. In addition, when comparing the murine line BHK-21 with the human cells (HepG2, Sk-Hep-1 and HKB-11), the latter showed to be able to produce rFVII more efficiently, which allows to conclude that human cell lines are a great alternative for the production of recombinant blood coagulation factors.

14 Claims, 17 Drawing Sheets

(56) References Cited

OTHER PUBLICATIONS

Ruiz, S. M. et al. Expression and purification of recombinant rabbit factor VII. Thromb Res. 2000. vol. 98, No. 2, pp. 203-211. doi: 10.10161S0049-3848(99)00227-3. Abstract, section Materiais e M~todos.

Seetharam, S. et al. Cloning and expression of rat coagulation factor VII. 2003. Thromb Res. vol. 109, No. 4, pp. 225-231. doi: 10.1016/S0049-3848(03)00149-X. Abstract, section "Materiais e Metodos."

Swiech, K. et al. Recombinant glycoprotein production in human cell lines. Methods Mol Biol. Janeiro de 2015. vol. 1258, pp. 223-240. doi: 10.1007/978-1-4939-2205-5J2. Abstract, pp. 229 and 233 to 239 (subitems 3.2 to 3.6).

Wajih, N. et al. Enhanced functional recombinant factor VII production by HEK 293 cells stably transfected with VKORCI where the gamma-carboxylase inhibitor calumenin is stably suppressed by shRNA transfection. Thromb Res. 2008. vol. 122, No. 3, pp. 405-410. doi: 0.1016/j.thromres.2007.11.002. Abstract, secao "Materiais e Metodos", first paragraph of section Results, Figure 2.

\* cited by examiner

METHOD FOR MODIFYING HUMAN CELL LINES TO PRODUCE FACTOR VII

FIELD OF THE INVENTION

The present invention is within the scope of application of Chemistry, Pharmacy, Medicine, Biotechnology and, more specifically, in the field of preparations for medical purposes since it relates to the process of producing blood coagulation factor VII in human cell lines.

BACKGROUND OF THE INVENTION

Coagulopathies

Hemophilia A is a blood disease linked to the X chromosome, caused by deficiency or abnormality of factor VIII (FVIII), a cofactor necessary for the generation of fibrin. This deficiency of coagulation protein is the most common among coagulopathies, with an incidence of approximately 1 in 5,000 men and is currently affecting approximately 400,000 people worldwide. Hemophilia B is a hereditary disease that is also associated with the X chromosome and consists of the deficiency of blood coagulation factor IX, with an incidence of 1 in every 30,000 men. Clinically, both hemophilia A and B present many similarities, that is, the patient presents frequent bleeding episodes, most of the time in cutaneous, musculoskeletal and soft tissue regions. Bleeding can also occur in other critical spaces, such as, for example, intracranial or retroperitoneal space.

Conventional therapy for patients with hemophilia consists of intravenous infusion of factor VIII or FIX derived from plasma or recombinant protein. However, one of the major problems is the formation of inhibitory antibodies against FVIII and FIX, which is currently, the most significant treatment-related complication in the clinical attendance of hemophiliac patients. Approximately 5% of patients with hemophilia B and 20 to 30% of patients with severe hemophilia A, submitted to FIX and FVIII replacement therapy, respectively, develop antibodies that inhibit the activity of the infused factor. The treatments available for these patients include the use of hemostatic agents and the induction to immunologic tolerance using high doses of FVIII or FIX infusions. These approaches are expensive because of the high cost of the factors, and not always successful. For this reason, many efforts have been made in an attempt to find an hemonstatic effective treatment, independent of the presence of factor VIII and IX.

Over the years, many studies have identified activated factor VII (FVIIa) as an attractive candidate for hemostasis, regardless of the use of FVIII/FIX in animal with hemophilia models. In addition, the FVIIa purified from plasma, has been shown to induce hemostasis in some patients having severe hemophilia. Taken together, these data suggest that pharmacological doses of FVIIa bound to the tissue factor (TF) exposed in the injury site, activate FX and promote the formation of thrombin in the injury site, causing this coagulation factor to present itself as an alternative for hemophiliac patients with inhibitory antibodies.

Mechanisms of Action of FVII in Normal Haemostasis and the Role of Pharmacological Doses According to the current concept, hemostasis occurs in two major types of surface: the cells that express tissue factor (TF) and platelets activated by thrombin and is initiated by the formation of a complex between the exposed TF and the FVIIa present in the circulation. FVII/FVIIa is the natural ligand of the tissue factor and the formed complex is fairly strong and stable.

Once the complex between TF and FVIIa is formed, the formation of a limited amount of thrombin occurs. This limited number of thrombin molecules formed in the initial phase of hemostasis activate the cofactors FVIII, FV, FXI and the platelets. Once activated, the platelets leave the circulation and go to the injury site. The activation of factors VIII and IX on the surface of activated platelets promotes activation of factor X in FXa, which in its turn binds to FVa generating a large amount of thrombin. The final step in the process is of a firm fibrin clot, which is resistant to premature proteolysis and is capable not only of initiating, but also of maintaining homeostasis, while the healing process is established.

In the absence of FVIII or FIX, only a small amount of thrombin is generated by the TF-FVIIa complex and the generation of total thrombin, which begins on the surface of platelets, does not occur. This last phase depends on the formation of the FVIII-FIX complex on the surface of the activated platelets. As a result, fibrin clots formed in hemophiliac patients are fragile and easily dissolved by premature proteolysis. From studies of hemophilia in cellular models, it was possible to demonstrate that pharmacological concentrations of recombinant factor VIIa (rFVII) bind non-specifically to activated platelets and generate thrombin on the surface thereof, even in the absence of FVIII/FIX. This occurs because rFVIIa activates FX on the surface of activated platelets independent of the presence of FVIII or FIX.

In this way, the addition of pharmacological doses of rFVIIa results in the rapid increase in the rate of thrombin generation on the activated platelet surface and as a result of increased activation of the platelets at the site of injury, increased adhesion platelets was observed, as well as other mechanisms necessary to maintain the homeostasis.

On Mar. 25, 1999 the FDA (Food and Drug Administration) approved the use of the first and only recombinant factor VII, NovoSeven®. Distributed by NovoNordisK, the recombinant activated factor VII (rFVIIa) is indicated in the treatment of bleeding episodes in patients having haemophilia A and B that develop antibodies against factors VIII and IX, respectively. In addition, rFVIIa is recommended for the treatment of critical spontaneous and/or surgical bleeding which threaten the lives of patients, as well as in patients with other diseases such as: FVII deficiency and Glanzmann's thrombasthenia.

Factor VII Gene

The factor VII gene has its locus located in region 34 of the long arm of chromosome 13 (13q34). Structurally and functionally, they are related to the group of vitamin K dependent serine proteases, which include factors IX, X, prothrombin (FII) and protein C. Its size is approximately 12.8 Kb and is composed of nine exons and eight introns. The nucleotide sequence of the exons is completely known. It is known that exons 1a and 1b and part of exon 2 encode a peptide signal that is removed during processing. The rest of the exon 2 and exons 3 to 8 encode a protein of 406 amino acids present in the blood circulation.

FVII is synthesized in the liver and circulates in the blood in a concentration of 0.5 µg/ml as a single chain, with a molecular weight of 50 kDa. In the amino-terminal moiety it consists of a domain rich in glutamic and γ-carboxylated acid (GLA domain), followed by two domains similar to epidermal growth factor (EGF), a short binding peptide and a serine protease domain in the carboxy-terminal moiety.

The conversion of factor VII to the active enzyme (FVIIa) occurs by the cleavage of the Arg152-Ile153 peptide bond, where no release of any peptide occurs. As a consequence, factor VIIa is composed of two polypeptide chains joined by disulfide bond. The light chain comprises the GLA domain, the aromatic helix and two EGF domains. This chain is composed of 152 amino acids that encode a protein of 20 kDa molecular weight. The heavy chain has the catalytic site of the molecule and comprises 254 amino acids with about 30 kDa molecular weight.

Factor VII and Vitamin K Dependent γ-Carboxylation

One of the main problems with the production of vitamin K-dependent recombinant coagulation factors for therapeutic use has been the deficient functional recovery of these proteins of the cell culture medium. Studies have shown that these results are mainly due to: 1) the incomplete γ-carboxylation of secreted proteins and 2) inefficient removal of the propeptide by Turin protease in the Golgi complex.

The vitamin K-dependent γ-carboxylation system is a system composed of several proteins located on the membrane of the endoplasmic reticulum. It consists of: 1) a vitamin K-dependent γ-carboxylase enzyme, which requires the reduced form of hydroquinone of vitamin. K (vit. K1H2) as cofactor and 2) the warfarin-sensitive enzyme, vitamin K 2,3-epoxide reductase (VKOR), which produces the cofactor. Concomitant with γ-carboxylation, hydroquinone is converted into the metabolite vitamin K 2,3 epoxide which is reduced back to the vit. K1H2 cofactor by the action of VKOR, in the so-called vitamin K cycle.

The calumeninee protein was identified as one of the factors capable of regulating the γ-carboxylation system, wherein the same would bind γ-carboxylase as an inhibitory chaperone and would also affect the VKOR protein. This conclusion is based on data that include: 1) the inhibition of γ-carboxylase activity with transfection of a construct containing the calumenine cDNA, 2) the silencing of the calumenine gene by a Smart siRNA and 3) a proteomic approach that demonstrates the existence of protein-protein interactions between β-carboxylase and calumenine. It has also been shown that when using Hek293 cells there was an increase in the production of recombinant FVII in these cells of 9% to 68%, when they were transfected for superexpression of the VKORC1 protein and concomitantly had the calumenine gene stably suppressed by more than 80% by the expression of a shRNA.

Within this context it is possible to predict that a human cell line has the proper machinery to γ-carbolixate and more efficiently produce recombinant FVII.

STATE OF THE ART

Documents US 2004023333, US 2010172891, BRPI 1105317-8 and "Expression of human coagulation factor VIII in a human hybrid cell line, HKB11" discloses the production of FVIII, different from the present invention which describes the production of FVII. It is worth noting that despite both participate in the blood coagulation cascade, factors VII and VIII are proteins that have different post-translational modifications and are classified into different protein families.

Document U.S. Pat. No. 4,784,950 describes the production of proteins from artificial plasmidial constructs that combine part of the protein of interest and part of factor VII. The present invention is directed to the production of FVII and in the construction of the recombinant DNA uses the integral FVII. The cited document uses murine (BHK) cells while the invention uses human cell lines.

Document US 2009088370 has the objective of increasing the secretion of the target proteins from the modification of the cultivation conditions. In this document it is reported that the cells are cultivated in specific conditions of serum-free medium with the addition of substances to the culture medium, mainly ionic substances. In the present invention, commercial means are used, chemically defined, with addition of bovine fetal serum and without addition of additional substances. Cells cited by the document: 293, 293T, 293F, 293H, Cos, CHO, NS0, insect cells. It does not mention any of the human cell lines used in the present invention.

Document US 2010331255 has as main objective increase the expression of the target protein by manipulating the cell gamma-carboxylation system. For this it uses as principal protein FIX and concomitant the expression of the target protein, overexpressing the VKORC1 gene and inhibiting of the inhibitory gene calumenine, using siRNA, in mouse cells (BHK). In the present invention, although the expression of the proteins bound to the gamma-carboxylation process is quantified, no methodology was used to intervene in the natural process of the cells.

Objectives and Advantages of the Invention

The objective of the present invention was to modify human cell lines with lentiviral vector containing blood coagulation FVIII cDNA and select the best recombinant FVII producing cell, to develop a bioprocess that enables the production of FVII in large scale using human cells.

This project had as innovation the use of human cell lines to produce rFVII more efficiently and, because it is human cells, to avoid the development of possible immunogenic epitopes expressed in murine cells, and finally to obtain a safer recombinant product. The use of murine cell lines offers disadvantages considering the complexity of post-translational modifications of FVII.

The need for a safer coagulation factor VII, with a reduced cost, and also, the need to develop new bioprocesses using efficient cell lines together with strategies that allow the production of high levels of products justified the realization of this project, which aims to develop an optimized bioprocess for factor VII production. Works in this sense can bring as benefits to the Brazilian society the possibility of obtaining more efficient medicines. In this context, the present invention has the purpose of cloning and expression of FVII in human cell lines for the production of an identical rFVII, especially in relation to the post-translational modifications, to that of human plasma.

BRIEF DESCRIPTION OF THE INVENTION

The present invention relates to the process of producing blood coagulation factor VII in 3 human cell lines (HepG2, Sk-Hep, HKB-11) and to select the best recombinant protein producer. The murine BHK-21 line was used as a control. Initially, the FVII gene (ATCC) was cloned into the bicistronic lentiviral vector p1054-CIGWS, which contains the GFP gene, which encodes a fluorescent protein, which allows observation of the modification efficiency of cell lines. After modifying the cells, the expression of gene marker GFP was observed by fluorescence microscopy and flow cytometry, in which 80% of BHK-21-rFVII cells presented GFP expression. HepG2-rFVII cells showed an expression of 73% whereas HKB-11-rFVII cells showed 32% of cells GFP positive. The Sk-Hep-rFVII cell line was the one that showed the better efficiency of transduction being approximately 95% of the modified cells. The next step consisted in characterizing rFVII produced by the modified cell lines. Quantification assays by the ELISA assay were done. The analyzes showed that in 48 h of culture, HepG2/rFVII cells produce about 1506 ng/ml rFVII, followed by SKHep/rFVII (951 ng/ml), HKB-11/rFVII (808 ng/ml) and BHK-21/rFVII (302 ng/ml). The same cell supernatant was used to verify the amount of FVII biologically active that the cell lines produced. After the coagulometric test HepG2/rFVII cells were found to produce of 1.07 IU/mL of biologically active rFVII, followed by SKHep/rFVII (0.56 IU/mL), HKB-11/rFVII (0.60 IU/mL) and BHK-21/rFVII (0.04 IU/mL) lines. In order to analyze the mRNA expression related to rFVII, as well as γ-carboxylation-related enzymes, a real-time PCR was performed. After analyzing the data, it was observed that the three modified human lines showed mRNA expression relative to rFVII. When undergoing treatment with vitamin K for a period of 10 passages in culture, rFVII gene expression was similar for the three lines (HepG2: 164563 ERU, HKB-11: 119122 ERU and Sk-Hep: 124919 ERU) which suggests that there was a stabilization in the expression levels of the recombinant protein. In relation to γ-carboxylation enzymes it was possible to observe that both γ-carboxylase, VKORC1 and the calumenine inhibitor presented increased levels of mRNA expression when treated with vitamin K, suggesting that it activates the enzymes of the cycle.

In this way, until now, the data allows to assert that the system used for the modification of cell lines was efficient, so that all cells were satisfactorily modified, and produced the protein of interest in a stable manner. In addition, when comparing the murine BHK-21 line with human cells (HepG2, Sk-Hep-1 and HKB-11), the latter showed to be able to produce rFVII in a more efficient way, which allows conclude that human cell lines are a great alternative to the production of recombinant blood coagulation factors.

of glucose and lactate during the culture of HKB-11-1-FVIIr in DMEM-F12 medium 10% SFB in spinner flasks (n=2).

Figure 22:
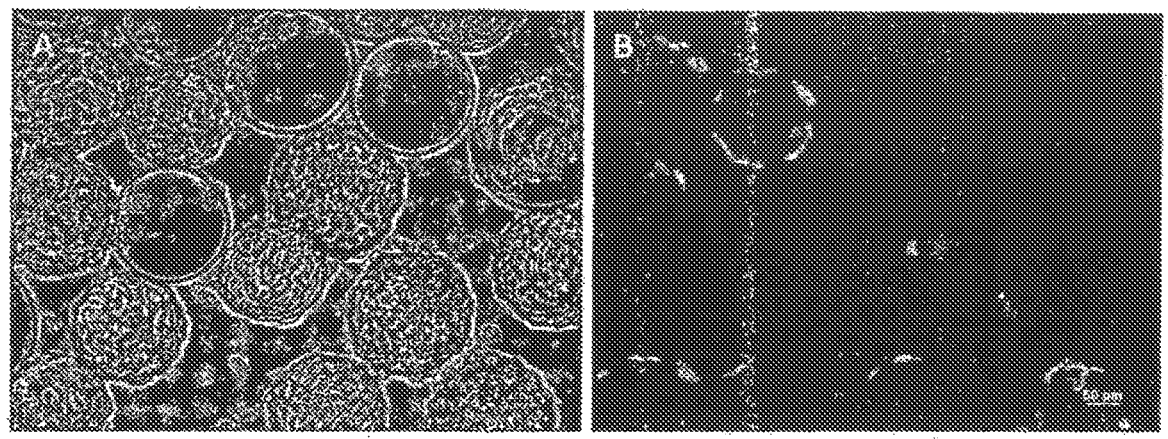

FIG. 22 shows the morphology of adhered HKB-11-FVIIr cells in microcarriers on the seventh day of experiment—in A, photomicrography in phase contrast, showing the adapted cells adhered to microcarriers; in B, electron microscopy of fluorescence showing GFP expression in adhered cells.

Figure 23:
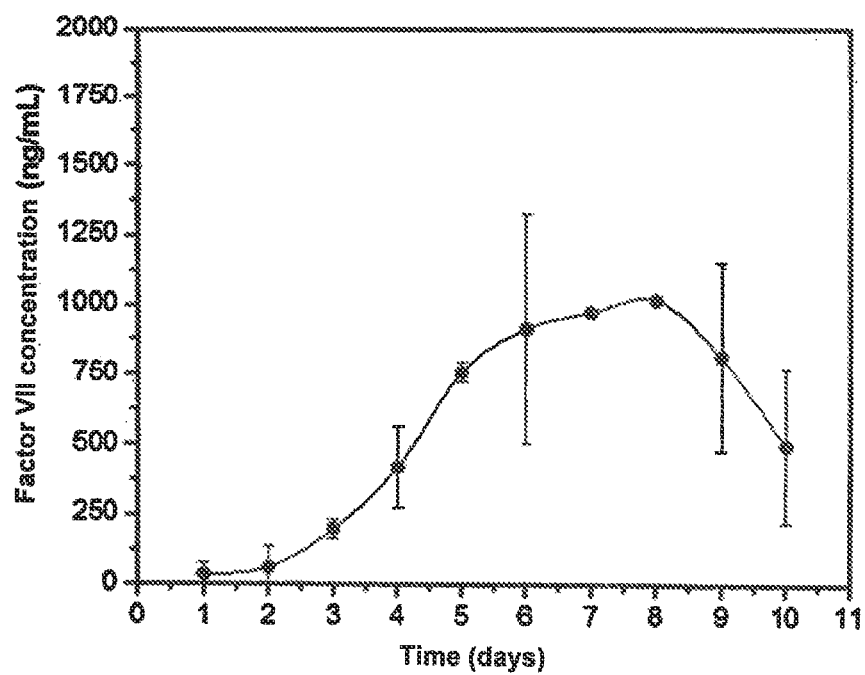

FIG. 23 graphically depicts the production kinetics of the recombinant factor VII HKB-11 cell line cultured for 10 days in spinner flasks.

Figure 24:
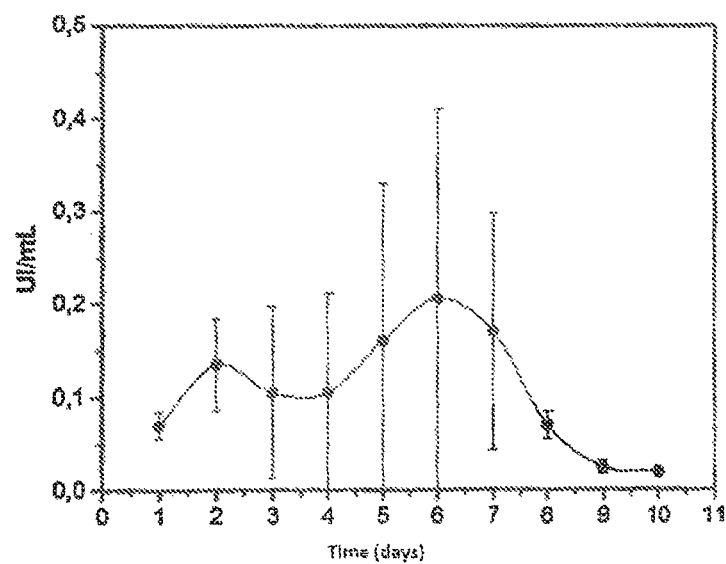

FIG. 24 graphically depicts the production kinetics of biologically active FVIIr in cultured HKB-11-FVIIr cell line in spinner flasks for 10 days.

Figure 25:
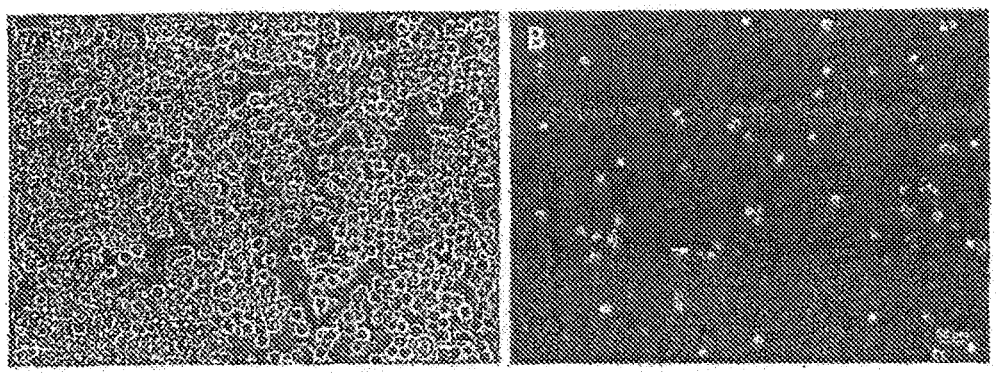

FIG. 25 shows the morphology of HKB-11/rFVII cells in third passage in bovine fetal serum free medium; in A, photomicrography in phase contrast, showing the cells adapted to the growth in suspension; in B, electron microscopy of fluorescence showing the GFP expression in the adapted cells.

DETAILED DESCRIPTION OF THE INVENTION

The present invention describes the process of producing blood coagulation factor VII comprising the steps of:

1) Obtaining virus particles containing FVII and the GFP protein as reporter gene—using lentiviral vector;
2) Transducing human cell lines, preferably, SK-Hep 1, HKB 11, and HepG 2 with viral particles to form FVII-producing cells;
3) Culturing human FVII-producing cells in suspension using microcarriers.

Transfection of the Hek293T cell line to produce viral particles was performed. For viral production it is important that the cell line (Hek293T) stably express the gene for the large SV40 T antigen. In this process it is necessary to use a vector containing the transgene and two auxiliary vectors, which have the origin of replication of SV40, so that after transfection the plasmids within of cells can replicate which increases transcription of the transgene and the production of viral proteins and ultimately viral particles will be secreted in the culture medium.

For the production of viral particles the reagent polyethylamine (PEI) was used. The three plasmids were transfected into the following proportion: 10 to 20 μg vector with transgene (p1054-rFVII), 8 to 15 μg pCMVΔR8.91 (containing HIV-1 gag, pol, ver and tat), 5 to 10 μg pMD2 VSVG (encodes the VSV-G shell).

After transfection (15 to 20 hours) the cells were incubated with cool medium. After 48 hours the supernatant was collected, centrifuged at 450×g for 5 minutes at 4° C., filtered (0.45 μm filter) for the removal of cell fragments. Aliquots of 1 ml were frozen at −80° C. for determination of viral titer and for use in transduction experiments. Once frozen at −80° C. and thawed (at 37° C.), the infection strength is decreased by about 20 to 40%. However, for standardization of use and for experiments may be replicable, the viral particles were primarily frozen.

For titration of the viral supernatant, it was initially plated $2\times10^5$ Hek293T cells in each well of the 6-well plate. After reaching 80 to 90% confluence, the cells were infected with the supernatant containing p1054-rFVII virus in the following dilutions: 1:1, 1:2 and 1:3, the ratio of viral supernatant being to fresh culture medium. The dilutions were made in duplicate and 5.5 ug/mL polybrene was used.

After 16 h of infection, the cell medium was changed to fresh medium (DMEM 10% bovine fetal serum). Cells were then cultured for 48 h and after this period were trypsinized and taken to flow cytometry for analysis of the expression of the GFP gene contained in vector p1054-rFVII. With the results obtained by the flow cytometry it was possible to calculate the viral titer.

Factor VII and GFP are not fused, they are separated by a IRES element; the method further comprises identifying the transduced cells and non-transduced cells by the presence of the GFP protein.

The supernatant produced by Hek293T cells that were previously transfected and frozen, were thawed and placed on the cultures of the Sk-Hep, HepG2, HKB11 and BHK, in the presence of 5.5 μg/mL polybrene. For this, 24 hours before of the transduction, the cells were plated at $2\times10^5$ cells per well in the 6-well plate. A virus concentration of 10 virus/cell, based on the values obtained by viral titration. After addition of the viral supernatant, the cells were incubated at 37° C. in a humid atmosphere containing 5% $CO_2$, and the transduction cycles were repeated for two to three consecutive days, depending on the cell line.

Initially the cells were cultured in culture flasks of 75 cm² for expansion, and incubated at 37° C. and 5% $CO_2$. After reaching the confluence of approximately 80%, the cells were released with Trypsin-EDTA and inoculated in 75 cm² T-flasks. The cellular morphology during expansion was observed with the use of an inverted microscope.

After reaching the sufficient number of cells ($5\times10^{<6>}$cells), was inoculated into spinner flask (100 to 150 mL, with work volume of 50 mL) already containing culture medium and microcarrier. The concentration of 2.0 to 4.0 g/L of CYTODEX 3 microcarrier was used. The preparation and sterilization of the microcarriers was performed according to the manufacturer's standards. The experiment was divided into 2 phases: the phase for adhesion and the phase for cell expansion. The duration of the adhesion phase was 6 hours with intermittent agitation: every 30 minutes for 2 minutes. For the expansion phase, constant stirring of 40 rpm was used.

In order to evaluate the cell adhesion in the microcarriers, samples were taken at each hour for cell density determination in suspension and viability.

To monitor cell growth during the expansion phase samples were taken every 24 hours for cell quantification and for further analysis of glucose, glutamine, lactic acid and ammonia. Free cells in suspension were quantified using method of exclusion by tripan blue dye. For the cells adhered in the microcarriers, the quantification was determined using of the Crystal Violet method.

Samples of the cell supernatant were collected, centrifuged and frozen at −20° C. for further ELISA analyzes and biological activity assay.

The experiment lasted 10 days, and every 3 days photomicrographs were performed under phase contrast microscopy to analysis of the cells adhered to the microcarriers and microscopy of fluorescence, for analysis of GFP expression of adhered cells.

For the adaptation step, the post-sorting of HKB-11 cell was used. Initially the cells were cultured in 75 cm² T-flasks in DMEM-F12 medium containing 10% bovine fetal serum. After reaching the confluence of 90%, the cells were trypsinized with trypsin-EDTA solution and $1\times10^6$ cells were plated in 25 cm² T-flasks with Free Style medium supplemented with Pluronic, ITS (Insulin, Transferrin and Selenium) and 10% (v/v) Penicillin/Streptomycin, in the absence of bovine fetal serum.

After 48 h, the cells were picked up, counted and viability observed by trypan blue reagent (0.4%). Again $1\times10^6$ viable cells were plated in 25 cm² T-flasks with Free Style medium supplemented. This procedure was performed by 5 passages, until the cells were adapted to the growth in serum-free and suspension-free medium.

This process produces about three times as much FVII protein than an amount of FVII protein normally found in human plasma.

Results

Characterization of Cell Lines

The human cell lines HepG2, Sk-Hep-1, HKB-11 and BHK-21 murine cell line, were cultured in an attempt to produce a master cell bank and a working cell bank. The cell bank production is of utmost importance because it allows that there is a reproducibility of the experiments over the project development.

Figure 1:
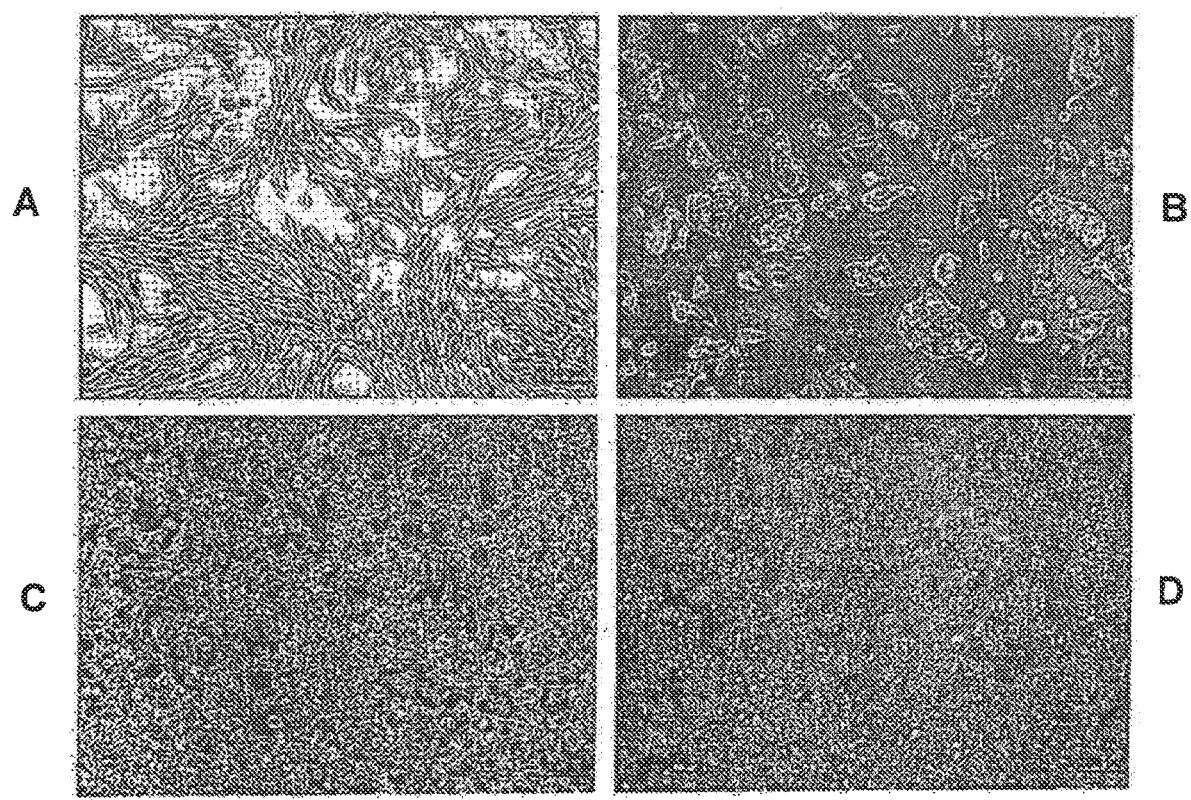
FIG. 1 shows the morphology of human cell lines—Photo in phase contrast optical microscope showing in (A) BHK-21 cell line, (B) HepG2 cell line, (C) HKB-11 cell line and (D) Sk-Hep-1 cell line.

In order to better understand the cell lines used in the present invention, a morphological characterization of the cells, by means of photos under optical microscopy of contrast of phase was performed (FIG. 1).

As can be seen in FIG. 1, cells from the murine BHK-21 (A) are large, with elongated morphology and fibroblast features. In B, it can be observed the HepG2 line that grows in clusters of cells adhered to the culture plate. This profile of growth is probably due to the fact that these cells derive from a hepatocarcinoma.

The hybrid cell line HKB-11 is shown in (C), in which can observe that the cells grow adhered and have a more elongated morphology, however, of smaller size, when compared to BHK-21. The Sk-Hep-1 (D) line presents morphology of epithelial cells, according to their origin hepatic adenocarcinoma.

Figure 2:
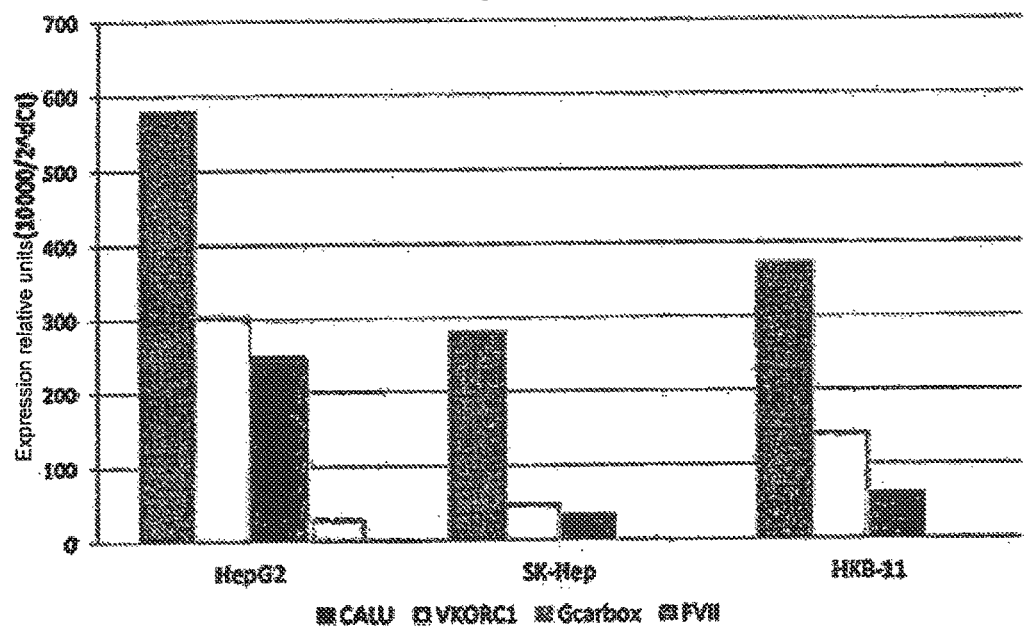
FIG. 2 graphically depicts the relative expression of the genes CALU, VKORC1, γ-carboxylase and FactorVII in human cell lines.

Besides the morphological characterization, the human cell lines were also characterized in terms of gene expression involved in the γ-carboxylation process. For this, the real-time PCR quantification of β-carboxylase genes and vitamin. K 2,3-epoxide reductase (VKORC1), in addition to the calumenine inhibitory gene (CALU). It was also possible to quantificate mRNA for the gene of endogenous Factor VII, as shown in FIG. 2.

In relation to the genes involved in the γ-carboxylation process, the HepG2 cell lines is the most expressing γ-carboxylase and VKORC1. HepG2 cells expressed 251 expression relative units (ERU) of the γ-carboxylase gene and 305 ERU of the VKORC1 gene. HKB-11 and SK-Hep cells express about 63 ERU and 35 ERU of gene γ-carboxylase and 144 ERU and 50 ERU of the VKORC1 gene, respectively.

As observed in the graph, the HepG2 lines were the one which most expressed the inhibitory gene CALU, in the order of 580 ERU, followed by HKB-11 (371 ERU) and SK-Hep (281 ERU) lines.

In order to select the best cell line for the production of recombinant factor VII, a ratio between the expression of the CALU inhibitory gene and the expression of the genes involved in γ-carboxylation (Table 1).

TABLE 1

Ratio between expression of CALU, VKORC1 and γ-carboxylase

| Cells | Ratio (CALU/VKORC1) | Ratio (CALU/γ-carbox) |
|---|---|---|
| HepG2 | 1.90 | 2.30 |
| SK-Hep | 5.54 | 7.85 |
| HKB-11 | 2.57 | 5.82 |

As shown in Table 1, the cell line that presented lower ratio between the expression of the inhibitory gene CALU and the γ-carboxylase and VKORC1 was HepG2, followed by the HKB-11 line.

After the characterization of the human cell lines, the next step consisted of the cloning of the factor VII gene. In view of the gene expression of the cell lines results, as well as literature data, the mRNA isolation of HepG2 cells was started, for subsequent cDNA production, gene isolation and cloning in the vector of expression.

Factor VII is a gene that, by the process of alternative splicing, presents 4 variants and one of them is not transcribed. The prevalent form in the normal liver is variant 2, which due to the alternative splicing process, does not contain exon 1b and thus encodes a small signal peptide. Variant 1 contains exon 1b, which thus encodes a longer signal peptide. However, the mature peptide coded by both variants are identical. The third variant shows the absence not only of exon 1b but also of exons 2 and 3 and, in this way, it generates a mature peptide that has no biological activity.

Thus, it was chosen to acquire the factor VII gene related to variant 2 and continue the experiments. This was cloned in the expression vector p1054-CIGWS. Viral vectors have as main advantage the insertion of the transgene into the DNA of the host cell, with which it passes to stably express the gene of interest.

The lentiviral vector used in this invention has the WPRE element which increases the efficiency of mRNA transport and processing, which probably contributed to a greater expression of FVII in the human cell lines.

Cloning of the FVII cDNA in a Lentiviral Vector

After cloning the FVII gene in the p1054 lentiviral vector, which culminated in the generation of p1054-rFVII vector, this vector was used for the production of viral particles. For the production of lentiviral vectors in Hek293T cells in addition to the vector containing the transgene, two other vectors, pCMVΔR 8.91 and pMD2.VSVG, responsible for the formation of the capsid and viral envelope, respectively, are also required to form viable particles. All vectors used were checked with restriction enzymes for confirmation of integrity.

With the three vectors checked, the triple co-transfection of the Hek293T cell line for the production of lentivirus using PEI reagent was performed.

Since the p1054 vector has the green fluorescence protein gene, GFP, it was possible to verify the transfection efficiency of cell line by means of fluorescence microscopy and flow cytometry.

Figure 3:
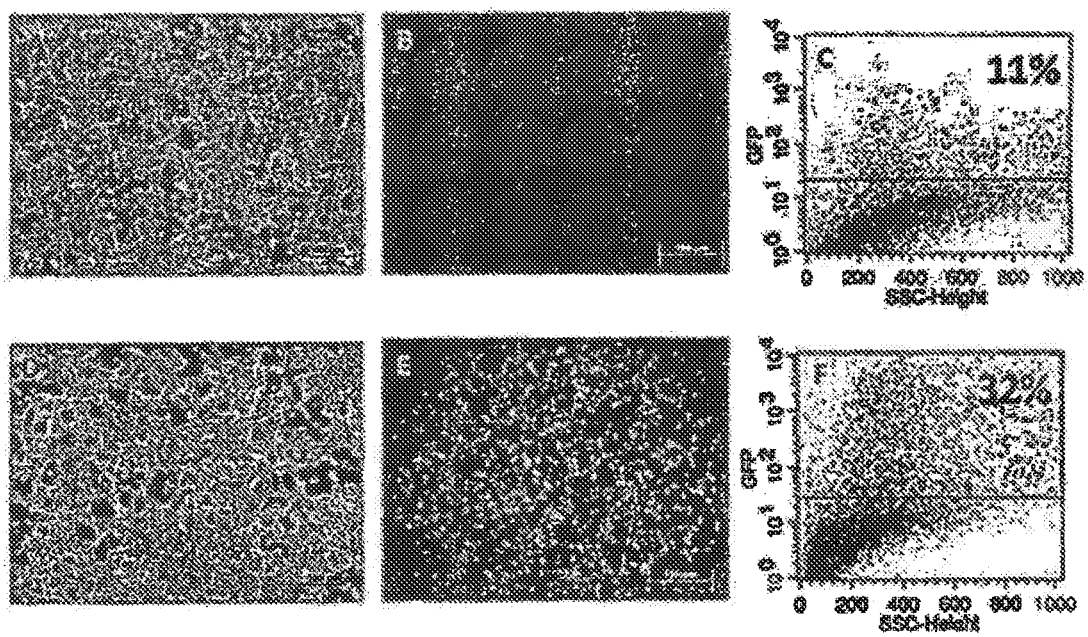
FIG. 3 shows Hek293T cells after 48 h of transfection with Lipofectamine® and with PEI—Photo in phase contrast optical microscope showing in (A and D) transfected Hek293T cell line; Photo in a fluorescence optical microscope showing in (B and E) Hek293T cells after 48 h of transfection using Lipofectamine® (B) and PEI (E); in C and F the percentage of GFP positive cells measured by flow cytometry can be observed.

As shown in FIG. 3, one can observe the photomicrography of Hek293T cells after 48 h of transfection with the PEI reagent. The percentage of positive GFP cells detected by flow cytometry was 32.17% (FIG. 3F).

After generation of the lentivirus producing Hek293T cell line, the next step consisted in collecting the cell supernatant containing the viral particles and titrating the amount of virus with intention to know exactly how many viruses would be used in the next step, the transduction of target cell lines.

To do so, the protocol previously described was used. 3 different dilutions of the viral supernatant were used and each made in duplicate. After 48 hours of infection, the cells were trypsinized and, since the p1054-rFVII vector has GFP, the percentage of infection can be observed by flow cytometry and subsequent calculation of viral title.

Figure 4:
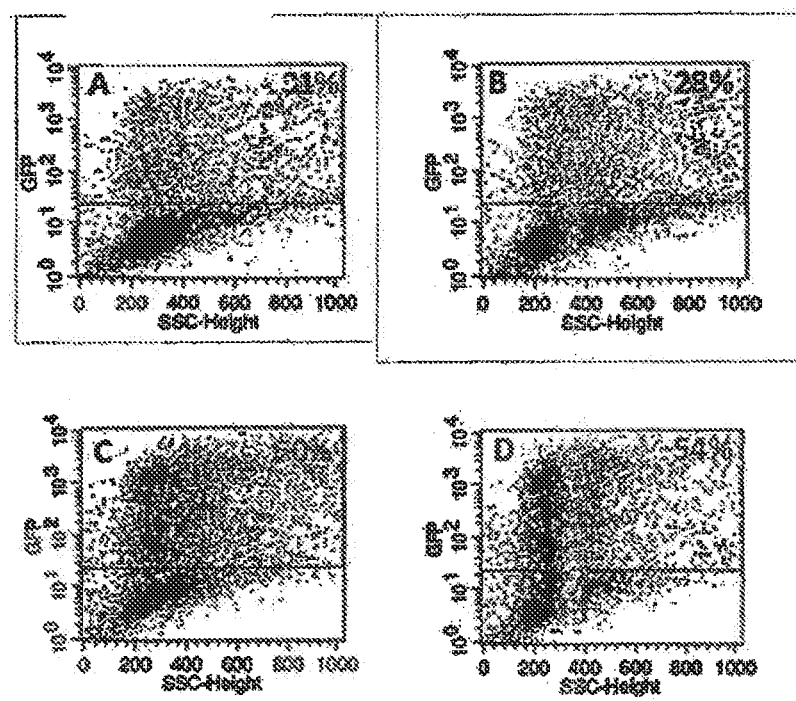
FIG. 4 graphically depicts the expression of GFP in Hek293T cells after 48 h of infection to calculate viral titre—Dilutions of viral supernatant—1:3 (A and B), 1:2 (C and D).

As shown in FIG. 4 the duplicates A and B, C and D relative to the dilutions of 1:3 and 1:2, respectively, can be seen.

For the purpose of calculating the viral titer the values for the 1:3 dilution were used. The calculated viral titre was $2 \times 10^6$ virus/ml.

Modified Cell Lines for rFVII Production

Figure 5:
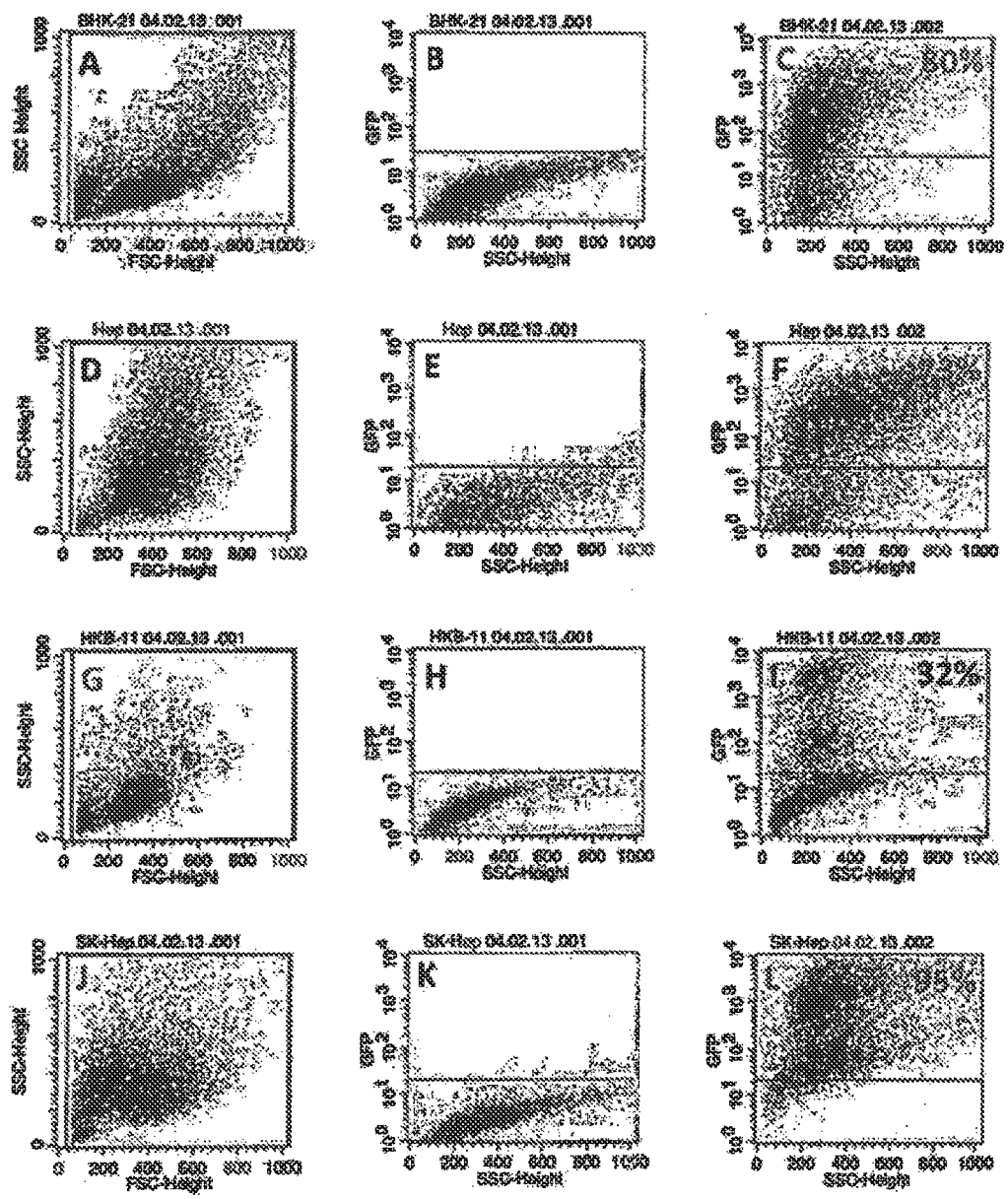
FIG. 5 graphically depicts the expression of GFP in recombinant cell lines BHK-21, HepG2, HKB-11 and Sk-Hep. In A, D, G and J dotplot showing size (FSC) by internal complexity (SSC) of the respective cells; in B, E, H and K dotplot showing the absence of GFP gene expression in control cells; in C, F, I and L dotplot showing GFP expression in cell lines modified with the vector p1054-rFVII.

After transduction with the viral supernatant, 4 cell lines modified with the vector p1054-rFVII were obtained, being them BHK-21 (murine), HepG2, Sk-Hep and HKB-11 (human). In order to verify if the modification had taken place satisfactorily, the expression of the GFP marker gene by flow cytometry was observed. As shown in FIG. 5, 80% of the BHK-21-rFVII cells presented GFP expression. HepG2-rFVII cells showed an expression of 73% whereas HKB-11-rFVII cells showed 32% of GFP. Sk-Hep-rFVII cell line was the one that showed the best efficiency of transduction, with approximately 95% of the cells expressed GFP after the modification.

Figure 6:
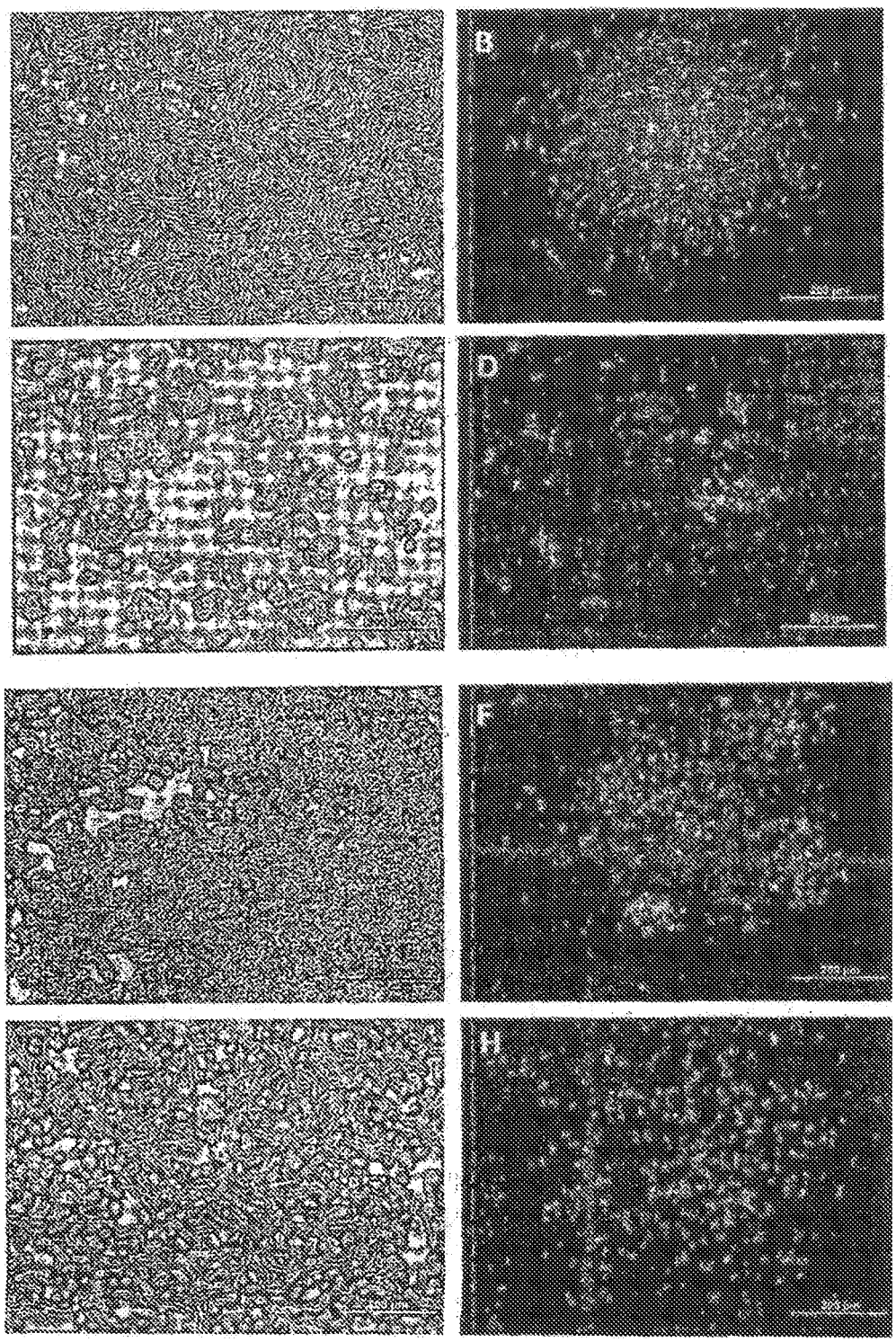
FIG. 6 shows recombinant cell lines modified with the vector p1054-rFVII; photo in phase contrast optical microscope showing in A, C, E and G the BHK-21, HepG2, HKB-11 and Sk-Hep cell lines, respectively; photo in optical microscope fluorescence showing the expression of the GFP gene in the BHK-21 (B), HepG2 (D), HKB-11 (F) and Sk-Hep (H) lines.

In order to verify the success of the modification of the cell lines, photomicrographs in a fluorescence optical microscope were made (FIG. 6).

Figure 7:
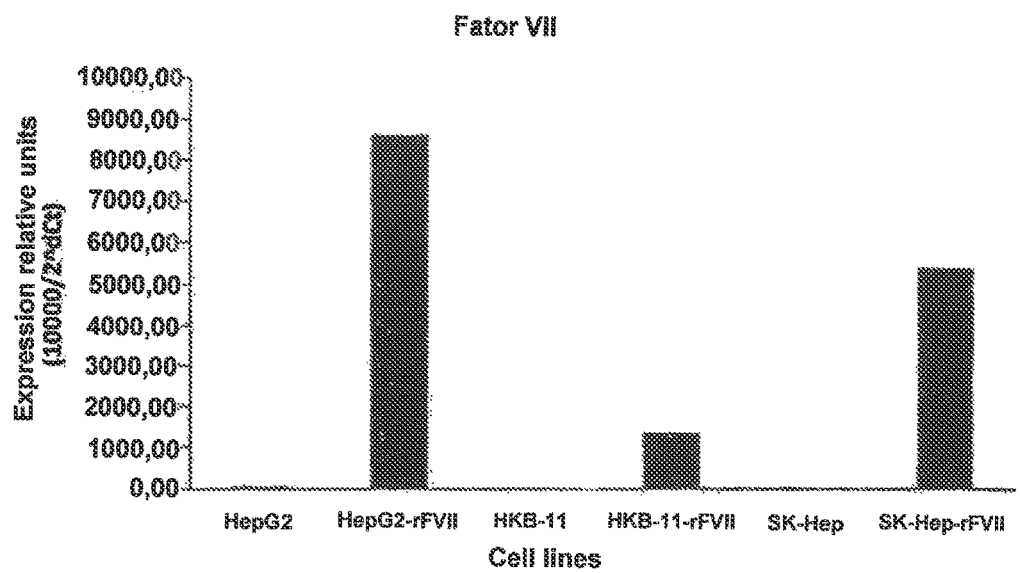
FIG. 7 graphically depicts the relative expression of the recombinant factor VII gene in human cell lines.

Characterization of Recombinant FVII Produced by Cell Lines Expression of rFVII in Modified Cell Lines After confirming the expression of the GFP gene by the flow cytometry and fluorescence microscopy methodologies, the next step consisted of analyzing mRNA expression related to the factor VII gene in human cell lines, HepG2, HKB-11 and Sk-Hep (FIG. 7).

As can be seen in FIG. 7, the three human cell lines expression of mRNA relative to the factor VII gene of the order of 8589 expression relative units (ERU) in HepG2-rFVII, 1361 ERU in HKB-11-rFVII line and 5357 ERU in Sk-Hep-rFVII cells.

These data show not only the efficiency in the modification of the cell lines, as shown by flow cytometry and by fluorescence microscopy, as well as the ability of these lines in expressing the recombinant protein of interest.

Quantification of rFVII in Modified Cell Lines

In order to quantify the total rFVII (active and non-active) produced by the modified cell lines, the ELISA assay was performed. To quantify the biologically active rFVII (rFVIIa) produced by the modified cell lines, the coagulometric test of prothrombin time (PT) was performed. The results of both tests are shown in Table 2.

TABLE 2

Quantification of FVIIr by the ELISA and PT assay

| Samples | Elisa (ng/mL) | Biological activity |
|---|---|---|
| HepG2 non-transduced | 6.3 | Nd |
| HepG2/FVIIr | 1176.57 (SD 465.65) | 1.02 (SD 0.19) |
| Sk-Hep non-transduced | 0.0 | Nd |
| Sk-Hep/FVIIr | 702.36 (SD 59.42) | 2.22 (SD 1.20) |
| HKB-11 non-transduced | 0.0 | Nd |
| HKB-11/FVIIr | 585.44 (SD 128.08) | 0.17 (SD 0.05) |
| BHK21 non-transduced | 0.0 | Nd |
| BHK-21/FVIIr | 222.60 (SD 112.71) | 0.16 (SD 0.04) |
| Human plasm | 500.0 | 1.0 |

As can be seen, the three human cell lines HepG2-rFVII, Sk-Hep-rFVII and HKB-11-rFVII showed amounts of rFVII levels higher than those found in human plasma, of the order of 1.7×, 1.5×, and 1.35×, respectively, showing that these lines are promising for the production of the recombinant protein.

In relation to actively produced rFVII, Sk-Hep/rFVII is the cell with the ability to produce more biologically active protein, followed by HepG2/rFVII, HKB-11/rFVII and finally the murine cell line BHK-21/rFVII.

Western Blot

After quantifying the recombinant protein by ELISA and verifying that the cell lines were producing biologically active FVIIr, a Western Blot was carried out in order to observe the size of the protein produced.

After checking the band pattern on the polyacrylamide gel, blotting was performed. For this, the gel content was transferred to a PVDF membrane and labeled with anti-FVII antibody (FIG. 8).

Figure 8:
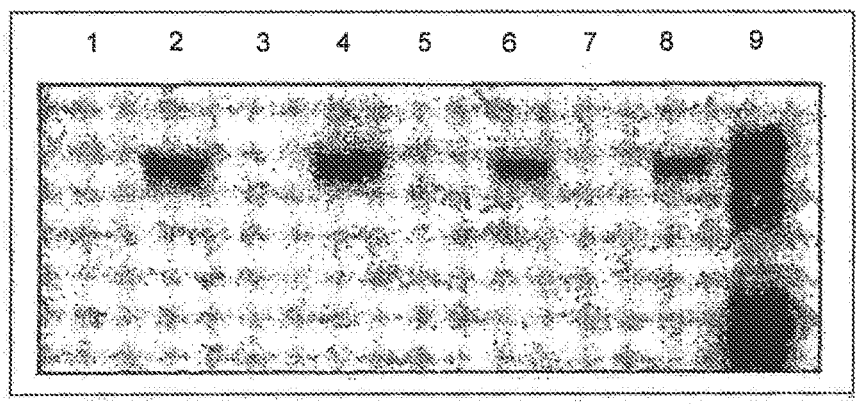
FIG. 8 shows Western Blot; 1—non-transduced HepG2, 2—HepG2/FVIIr, 3—non-transduced Sk-Hep-1, 4—Sk-Hep-1 FVIIr, 5—non-transduced HHK-11, 6—HKB-11/FVIIr, 7—non-transduced BHK-21, 8—BHK-21/FVIIr, 9—Novo Seven.

As it can be seen in FIG. 8, the bands of approximately 55 kDa evidenced the expression of the recombinant protein in the modified cell lines (lanes 2, 4, 6 and 8), whereas there is no expression of FVIIr in non-transduced cells (lanes 1, 3, 5, 7).

It can also be observed that cells that have higher mRNA expression related to FVIIr, as well as greater quantification in ELISA, are the cells that present bands of greater intensity in the Western Blot (HepG2-FVIIr on lane 2 and Sk-Hep-1-FVIIr on lane 4). Similarly, cells with lower mRNA expression and lower quantification in the ELISA, present bands related to FVIIr of weaker intensity values in Western Blot (HKB-11-FVIIr on lane 6 and BHK-21-FVIIr on lane 8).

On lane 9 the Novo Seven that was used as positive control of the reaction can be observed. The higher molecular weight band refers to unactivated single chain FVII (50 KDa), and the lower weight band (20 KDa) refers to the activated FVIIr light chain. The band of 30 KDa, referring to the heavy chain of FVIIr, does not appear in blotting since a monoclonal antibody that does not label this chain specifically was used.

Generation of Homogenous HKB-11/rFVII Cell Population

As shown previously, the HKB-11 cell line was the one which presented the lowest modification efficiency, after which the transduction only 32% of the cells were expressing the GFP marker gene, whereas the Sk-Hep, HepG2 and BHK-21 expressed 95%, 73% and 80%, respectively.

After 12 months of culturing, used for the establishment of cell lines, the percentage of cells that expressed GFP was followed (Table 3).

TABLE 3

Decrease in GFP percentage after 12 months of culture

| Cell line | % of GFP after transduction | % of GFP after 12 months of culture |
|---|---|---|
| Sk-Hep-rFVII | 95% | 80% |
| HKB-11-rFVII | 32% | 16% |
| HepG2-rFVII | 73% | 50% |
| BHK-21-rFVII | 80% | 64% |

As can be seen in Table 3, the HKB-11 cells were those that presented greater loss in the expression of the GFP marker gene, around 50%.

Figure 9:
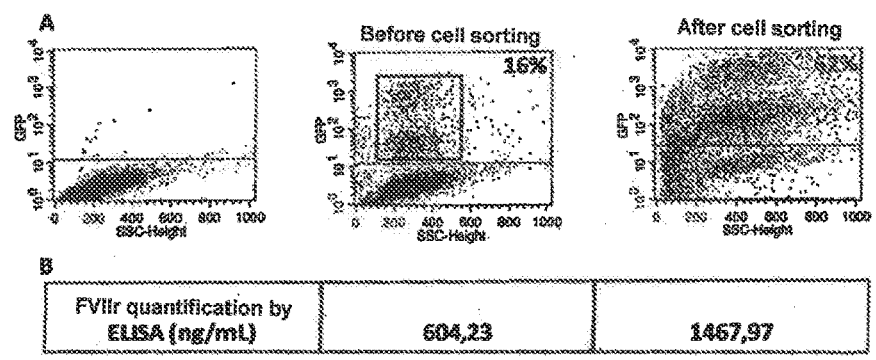
FIG. 9 graphically depicts GFP expression and quantification of FVIIr in the recombinant cell line HKB-11 before and after sorting—In graphic A showing size (FSC) by internal complexity (SSC), followed by the GFP expression graphic in the cell lines modified before the sorting; from the gate performed, in the last graphic it can be seen an enrichment in the number of cells expressing GFP after the cell sorting—in B, quantification of FVIIr by ELISA, before and after cell sorting.

With the aim of generating a more homogeneous population and with levels of expression more comparable to other cell lines shown in this invention, the selection of positive GFP HKB-11 cells was performed by cell sorting, which is shown in FIG. 9.

As observed, there was an increase in the number of cells that express GFP on the order of 3.9 times. These data were also confirmed by fluorescence microscopy.

In addition to the increase in the percentage of positive GFP cells, it was possible to observe an increase in the amount of rFVII produced, when the supernatant was assayed by ELISA test. After a period of 96 hours culture, non-sorting cells were producing 604 ng/mL of rFVII, while the post-sorting cells, cultured under the same conditions, produced 1468 ng/mL. From these results, the following experiments were used, only post-sorting HKB-11/rFVII cells, cited as HKB-11/rFVII.

Characterization of rFVII-Producing Cell Lines

To date, results have been presented related to the generation of recombinant FVII-producing cell lines, as well as an overall characterization of the protein at the level of expression, biological activity and western blot.

The following results refer to the characterization of the recombinant cell lines with the intention of selecting the best rFVII producer.

Modified Cell Lines Express rFVII mRNA and γ-Carboxylation Enzymes

Initially, mRNA expression analysis was performed related to the factor VII gene and the γ-carboxylase enzymes, VKORC1 and calumenine.

In order to analyze the expression profile, only the human cell lines HepG2, HKB-11 and Sk-Hep in four different conditions were used: 1) without transduction and without treatment with vitamin K, 2) without transduction and treated with 5 μg/mL vitamin K, 3) transduced with vector 1054-rFVII and without treatment with vitamin K and 4) transduced with 1054-rFVII vector and treated with 5 μg/mL vitamin K.

Figure 10:
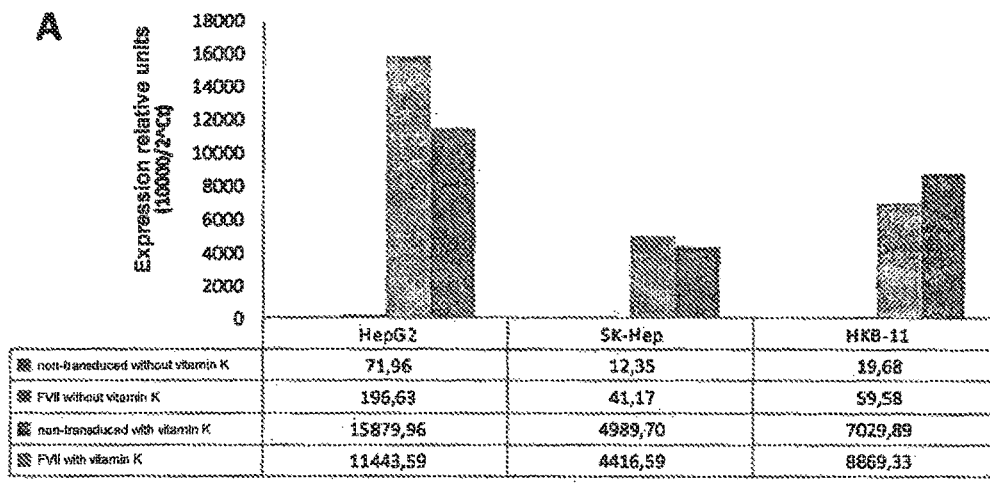
FIG. 10 graphically depicts the relative expression of mRNA relative recombinant Factor VII gene in human cell lines HepG2, HKB-11 and Sk-Hep.
Figure 10:
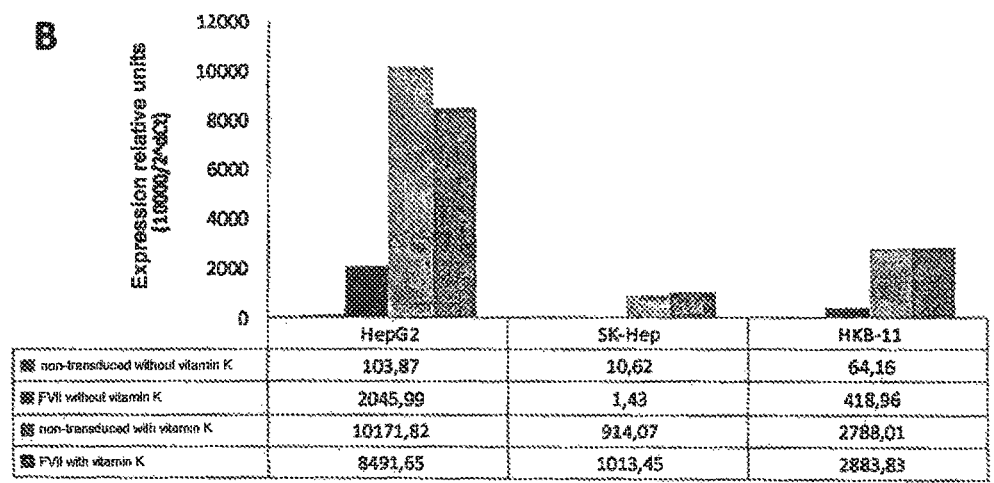
Figure 10:
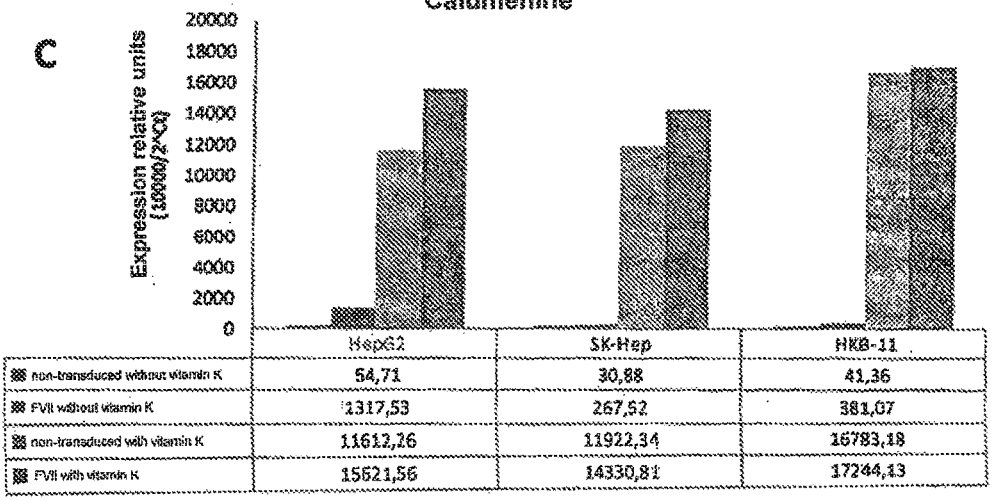

After analyzing the data, it can be observed that the three human lines presented mRNA expression related to recombinant FVII, after lentiviral vector transduction. When submitted to the treatment with vitamin K for a period of 10 passages in culture, the cells showed a similar expression (HepG2: 164563 URE, HKB-11: 119122 ERU and Sk-Hep: 124919 ERU) showing a stabilization in the expression levels of the recombinant protein (FIG. 10).

It is possible to observe that non-transduced HepG2 cell line, because it is derived from a hepatocarcinoma, expresses levels of endogenous FVII mRNA (as shown above) and that the expression of this endogenous FVII is increased by 480 fold when cells are treated with vitamin K.

Figure 11:
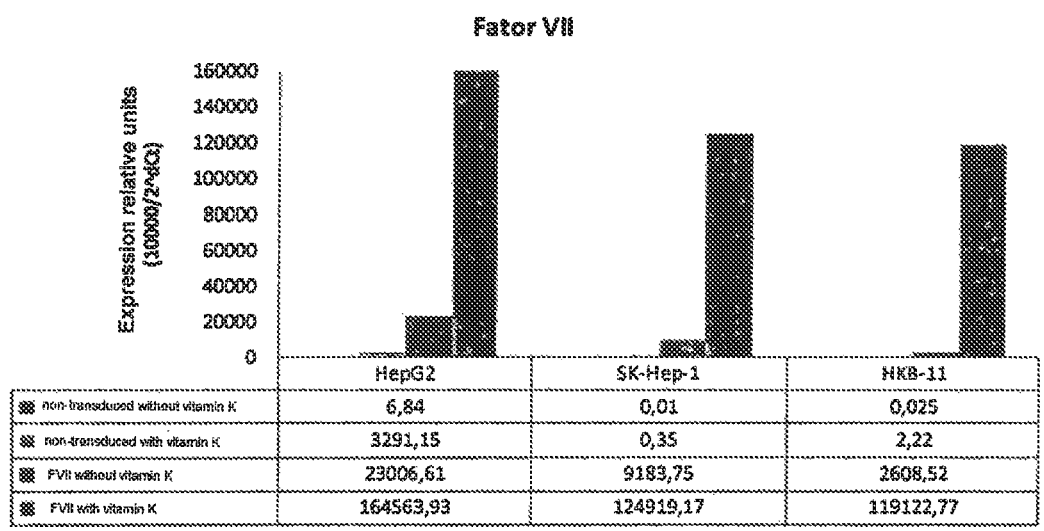
FIG. 11 graphically depicts the relative expression of mRNA related to γ-carboxylase enzyme gene, VKORC1 and calumenine inhibitory protein in human cell lines HepG2, Sk-Hep-1 and HKB-11, before and after transduction, before and after treatment with vitamin K.

When the expression of the enzymes related to γ-carboxylation was analyzed, it was possible to observe that there was a difference in the expression levels of γ-carboxylase enzymes, VKORC1 and the inhibitor calumenine (FIG. 11).

As seen in FIG. 11, when the cells were treated with 5 ug/ml vitamin K, there was an increase in the expression level of enzymes. When comparing treated and untreated non-transduced cells, it can be observed that in HKB-11 cells the expression of mRNA of the VKORC1 gene increased 43-fold (from 64 to 2788 ERU); γ-carboxylase expression increased 351-fold (from 20 to 7030 ERU) and the expression level of calumenine mRNA increased 409 fold (from 41 to 16783 ERUs). In SK-Hep-1 cells the expression of the mRNA of VKORC1 gene increased 91 fold (from 10 to 914 ERU), γ-carboxylase increased 416 fold (from 12 to 4989 ERU) and the calumenine inhibitory gene increased 397 fold (from 30 to 11922 ERU). In HepG2 cells the expression of the mRNA of the VKORC1 gene increased 98 times (from 104 to 10172 ERUs); γ-carboxylase expression increased 220 (from 72 to 15880 ERU) and the level of mRNA expression of the calumenine increased 211 fold (from 55 to 11612 ERU).

The same pattern of expression can be observed in the cell lines modified with FVII before and after treatment with vitamin K. In the HKB-11-FVII cell line the expression of the VKORC1 mRNA increased 7 fold (from 418 to 2883 ERU), γ-carboxylase increased 150 fold (from 59 to 8869 ERU) and the expression level of calumenine gene mRNA increased 54 fold (from 318 to 17244 ERU). In the Sk-Hep-1-FVII cells the expression of γ-carboxylase increased 108-fold (from 41 to 4416 REU) and the expression level of calumenine mRNA increased 54 fold (from 267 to 14331 ERU). In HepG2-FVII cells an increase of expression of VKORC1 (from 2045 to 8491 ERU) was observed, the expression of γ-carboxylase mRNA increased 58 fold (from 197 to 11443 ERU) and the expression level of calumenine gene mRNA increased 12 fold (from 1317 to 15621 ERU).

Growth Kinetics of Cell Lines

With the aim to evaluate the growth profile of recombinant factor VII-producing Sk-Hep, HBK-11 and BHK-21 cell lines the experiments were carried out for a period of 7 days, in duplicate.

Figure 12:
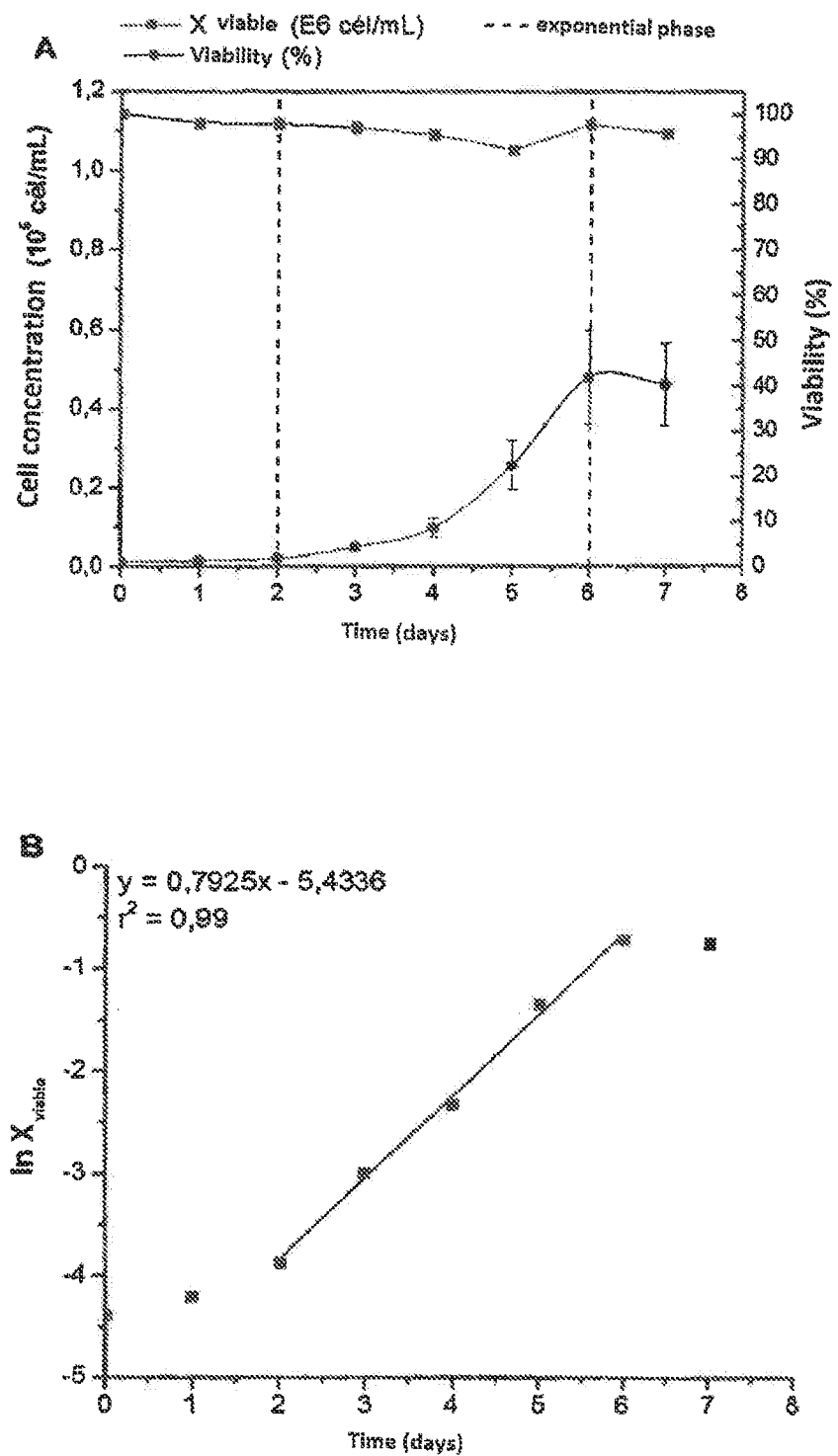
FIG. 12 graphically depicts the growth kinetics of SK-Hep-1-FVIIr cell line in A, cell growth and viability during the culture of Sk-Hep-1-FVIIr cells in DMEM medium with 10% SFB, in 10 cm$^2$ plates; in B, the specified maximum speed of growth ($\mu x \cdot max=0.79$ day$-1$) (n=2).
Figure 14:
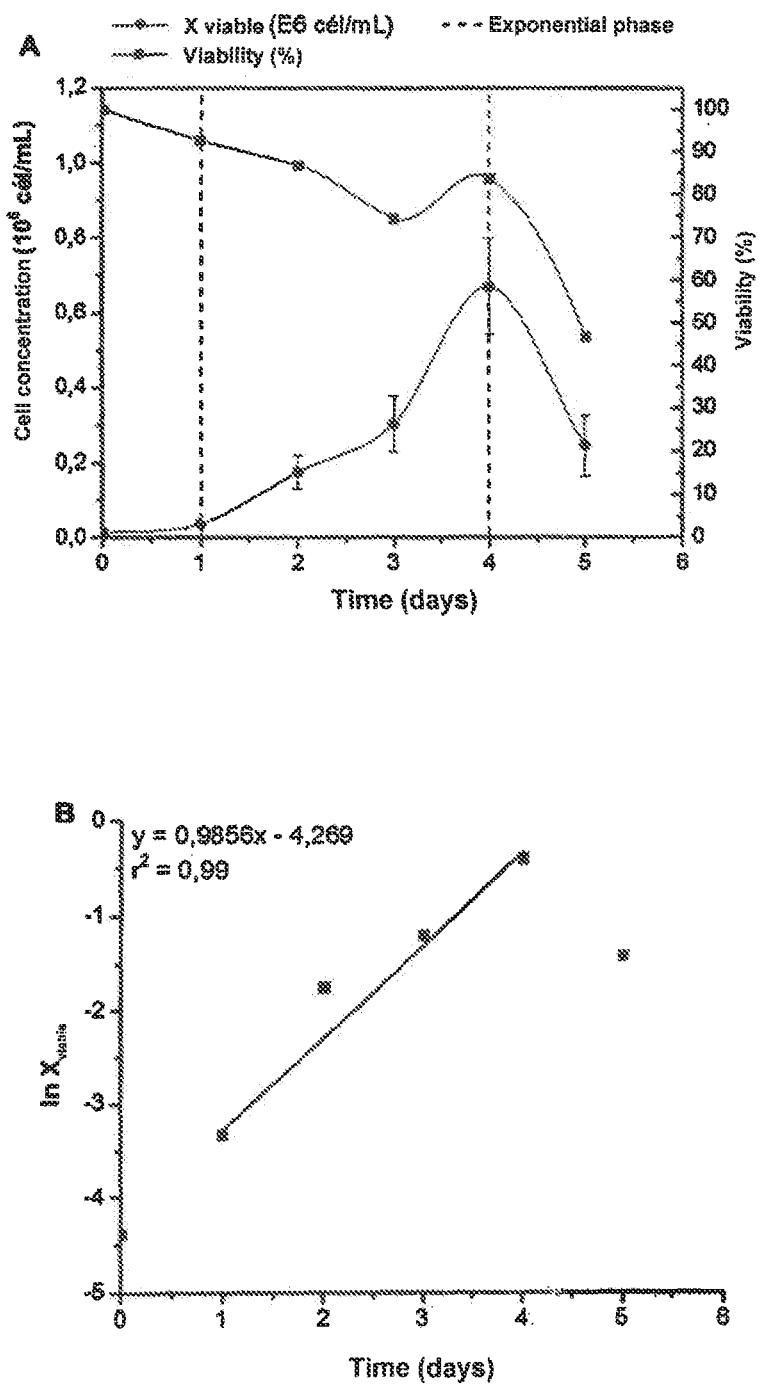
FIG. 14 graphically depicts the growth kinetics of BHK-21-FVIIr-A cell line, cell growth and viability (A) during the culture of BHK-21-1-FVIIr cells in EMEM medium with 10% SFB, in 10 cm$^2$ plates; in (B), the specified maximum speed of growth ($\mu x \cdot max=0.98$ day$-1$) (n=2).

FIG. 12 allows to observe that the Sk-Hep cell presented high viability, around 95%, throughout the whole analyzed period. The maximum cell concentration was $0.48 \times 10^6$ cells/mL achieved at sixth day of experiment. The exponential phase of growth occurred between days 1 and 6 and the maximum specific rate of growth (μx, max) was 0.72 day$^{-1}$, as shown in FIG. 14. It can be observed that after this period there is still cell growth, however, with a lower speed.

Figure 13:
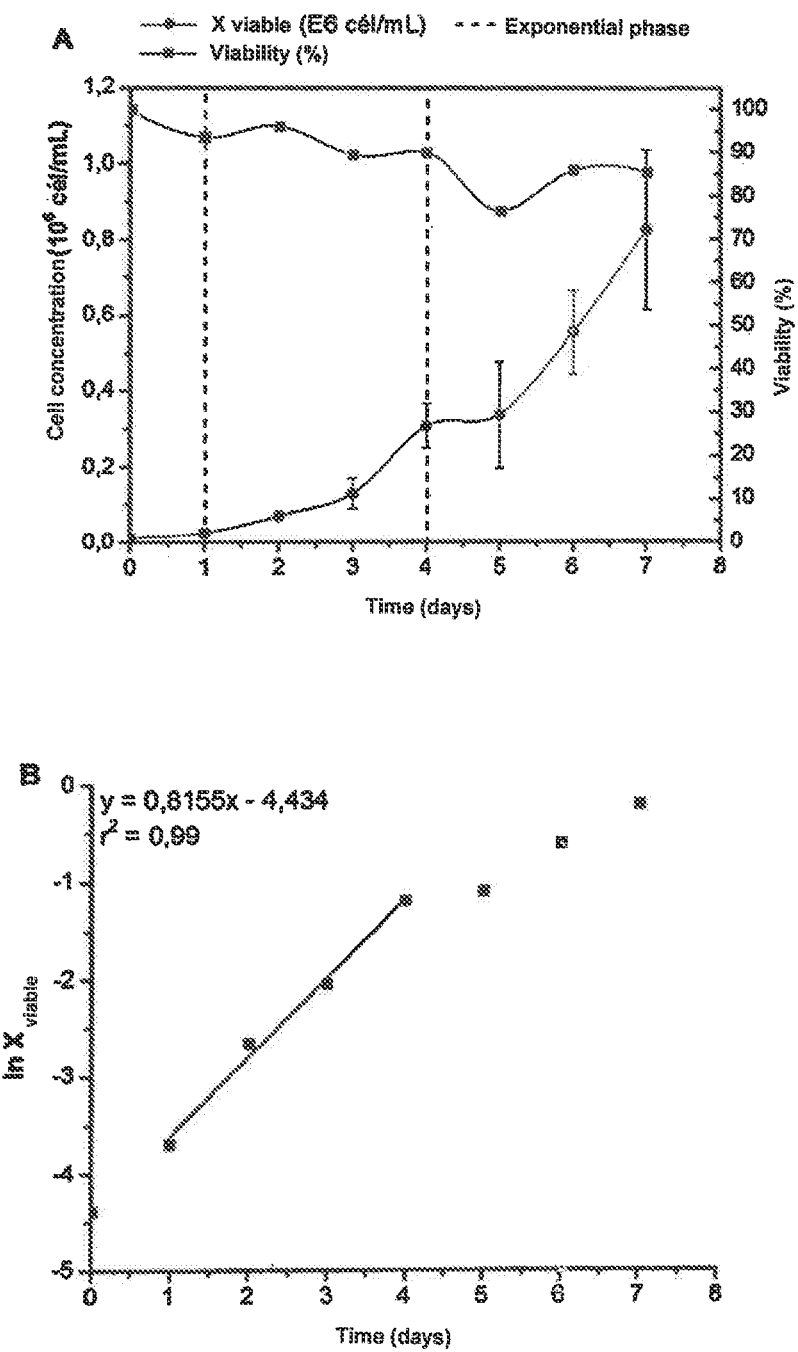
FIG. 13 graphically depicts the growth kinetics of HKB-11-FVIIr-A cell line, cell growth and viability (A) during the culture of HKB-11-1-FVIIr cells in DMEM-F12 medium with 10% SFB, in 10 cm$^2$ plates; in (B), specific maximum speed of growth ($\mu x \cdot max=0.81$ day $-1$) (n=2).

With the analysis of FIG. 13 showing the data related to HKB-11 cell line, it was possible to observe that these cells presented viability, around 90%, during the first four days of experiments, followed by about 80% in the last three days. The maximum cell concentration was $0.82 \times 10^6$ cells/mL achieved on the seventh day of the experiment. The exponential phase of growth occurred between days 0 and 4 and the maximum specific growth speed (μx, max) was 0.80 day$^{-1}$.

Then the data from the BHK-21 cell were analyzed (FIG. 14).

The BHK-21 murine line (FIG. 14) showed a viability around 92% on the first day, which declined over the experiment, leading to cell death on the sixth day. The maximum cell concentration was $0.67 \times 10^6$ cells/mL achieved on the fourth day of experiment. The exponential growth phase occurred between days 0 and 4 and the maximum specific growth speed (μx, max) was 1.0 day$^{-1}$. After this period, the cells entered the process of cell death.

Production Kinetics of rFVII in Cell Lines

In addition to the growth curve, assays in a 100 mm$^2$ plate with the same cell lines were also performed with the objective to evaluate the production of recombinant factor. VII. To this end, the initial concentration of cells was higher than that used in growth kinetics experiments.

Figure 15:
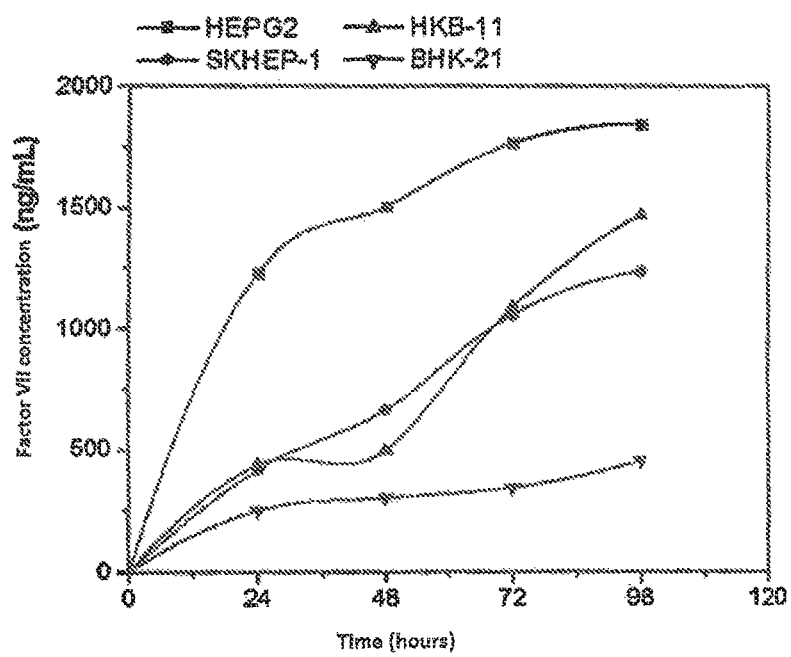
FIG. 15 graphically depicts the production kinetics of the recombinant factor VII producing cell lines; quantification performed by the ELISA test.
Figure 16:
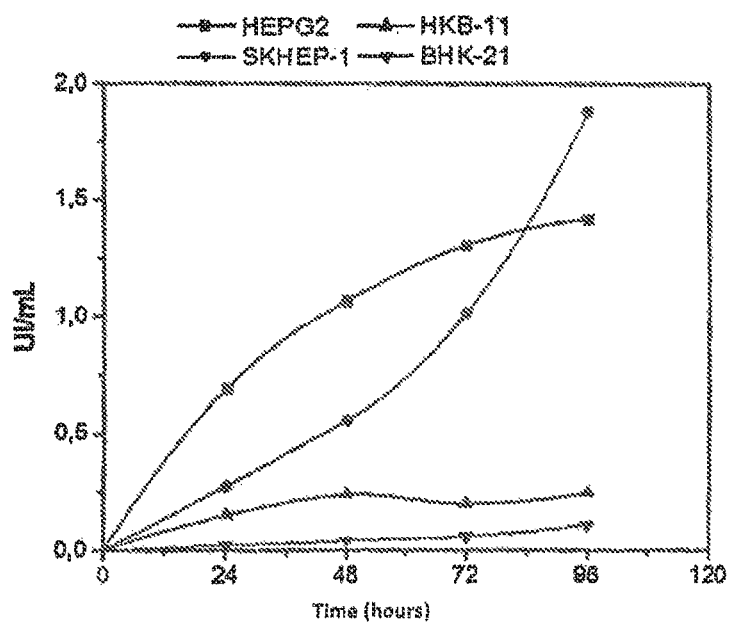
FIG. 16 graphically depicts the production kinetics of the recombinant factor VII producing cell lines, measured by thromboplastin time (PT) method.

FIG. 15 shows a graphic of the concentration of FVII (ng/mL) by time, of the three human cell lines and the murine line BHK-21.

When analyzing the amount of rFVII after the experiment period, it was possible to observe that HepG2 cells showed higher production of recombinant protein, whereas in 24 h had a production of 1227 ng/mL, reaching 1843 ng/mL, after 96 h of culture. As the cells were cultured in. 8 ml of medium, it was possible to produce a total of 14.7 μg of rFVII, which corresponds to 29.5 IU.

Sk-Hep cells had a production of 415 ng/mL in 24 h, reaching a total of 1432 ng/mL after 4 days. The HKB-11 line showed a similar production profile when compared to Sk-Hep, whereas on the first day there was an amount of 435 ng/ml of rFVII and at the end of 96 h it was possible to quantify about 1468 ng/mL. As there was 8 ml of culture medium in the plate, it was possible to produce a total of 11.7 µg of rFVII, which corresponds to 23.5 IU of the cells HKB-11 and 11.4 µg of rFVII, corresponding to 22.9 IU in Sk-Hep cells.

The BHK-21 murine cell line was the one with the lowest production of rFVII throughout the experiment, and in 24 hours there were 250 ng/mL and at the end of 96 hours only 449 ng/mL, totaling in 8 mL a production of 3.6 µg of rFVII, which corresponds to 7.2 IU.

Production of rFVII in Sk-Hep and HKB-11 Cell Lines in Spinner Flasks

Analysis of the previous results showed that the HepG2 cells have an extremely slow growth pattern, which made it impossible to use it in the subsequent stage of the work. The lineage BHK-21, of murine origin, is not the focus of the present invention, being used only as a control. In this way, the two FVIIr-producing human cell lines, which were used for subsequent experiments of suspension culture are Sk-Hep-1-FVIIr and HKB-11-FVIIr.

The experiments were carried out for a period of 10 days to analyze the growth profile, as well as the production of FVIIr in the cell lines growing in suspension using microcarriers in spinner flasks. The experiments were carried out in duplicate and the results are presented as an average of both.

In analyzing the data it was possible to observe that the Sk-Hep-1-FVIIr cell reached the maximum cellular concentration, in the value of $1.11 \times 10^6$ cell/mL, on the tenth day of the experiment. The exponential phase of growth occurred between days 1 and 6 and the maximum specific speed of growth (µmax) was 0.35 day$^{-1}$.

Figure 17:
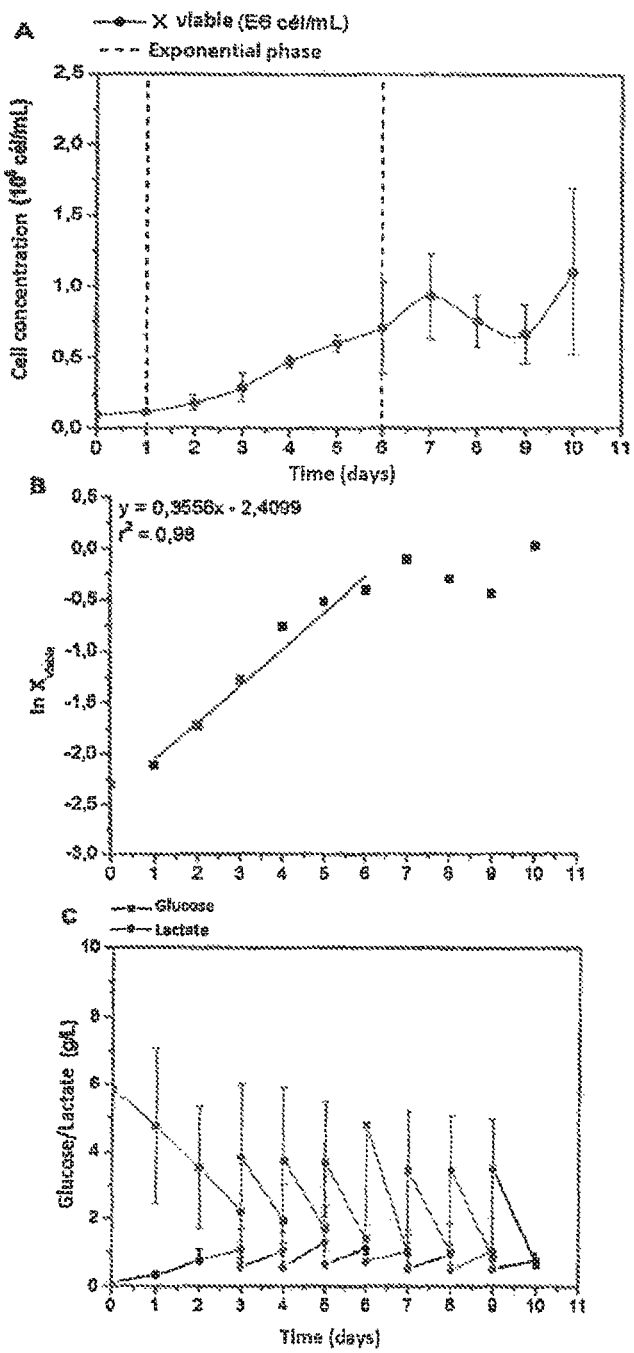
FIG. 17 graphically depicts the culture of the cell line Sk-Hep-FVIIr in microcarriers in spinner flasks—cell growth (A), specific maximum growth speed (B) and concentration profile (C) of glucose and lactate during culture of the Sk-Hep-1-FVIIr in DMEM medium 10% SFB in spinner flasks (n=2).

During the 10 days of culture it was possible to observe a gradual consumption of glucose, as was to be expected, however, there was no depletion due to 50% changes in the culture medium every 24 hours. In relation to lactate production, it was observed that this reached maximum concentration on the fifth day of culture, with the mean value of 1.25 g/L (FIG. 17).

Figure 18:
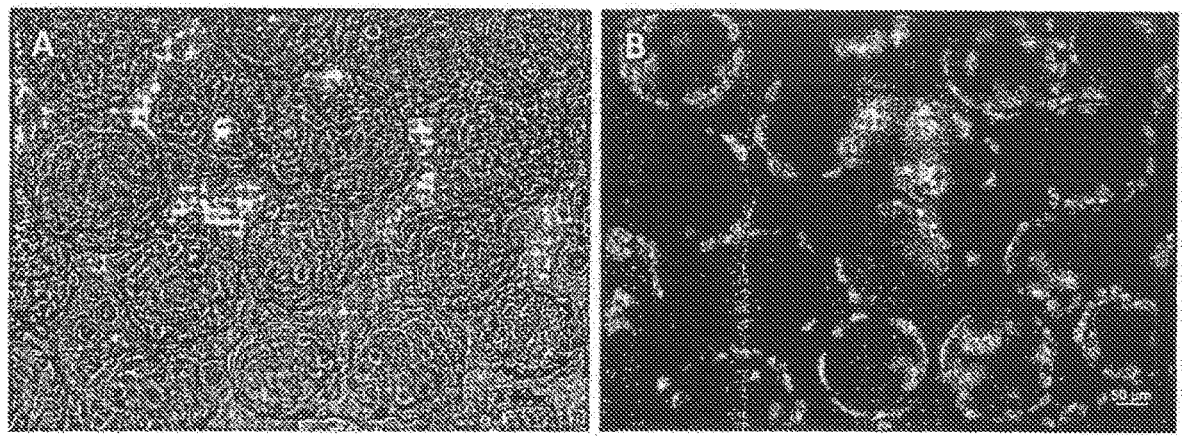
FIG. 18 shows the morphology of Sk-Hep-1-FVIIr cells adhered in microcarriers on the seventh day of experiment—in A, photomicrography in phase contrast, showing the adapted cells adhered to microcarriers; in B, electron microscopy of fluorescence showing the GFP expression in the adhered cells.

To illustrate the culture in microcarriers and expression of the GFP marker gene, images were taken with microscopy of phase contrast and fluorescence, as shown in FIG. 18.

Figure 19:
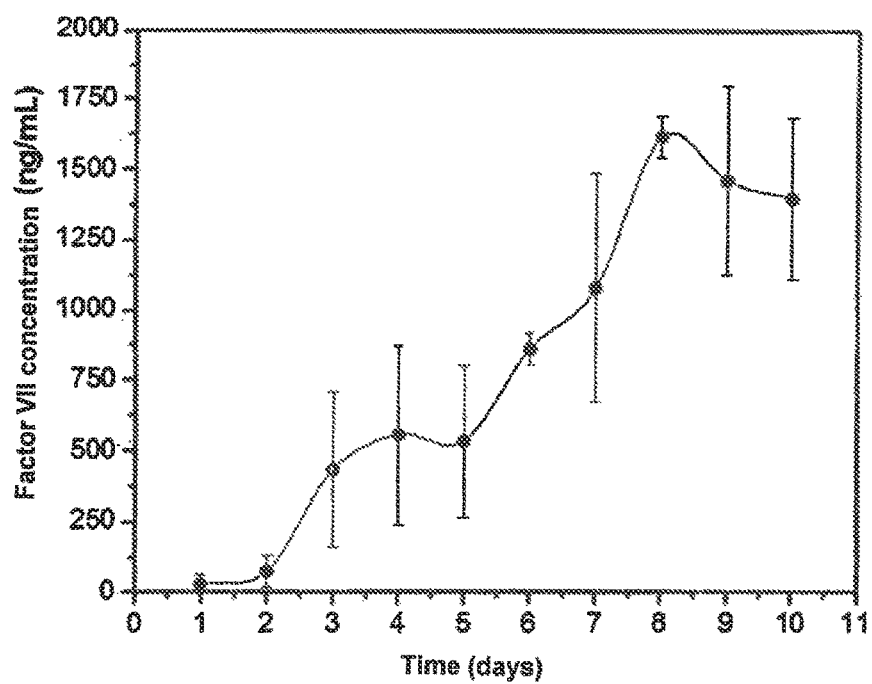
FIG. 19 graphically depicts the production kinetics of recombinant factor VII producing Sk-Hep-1 cell line cultured in spinner vials for 10 days.

In order to quantify the production of FVIIr by the Sk-Hep-1-FVIIr cell an ELISA assay was performed. As shown in FIG. 19, the production had its maximum peak reached on the eighth day of experiment, reaching an average concentration of 1615 ng/ml (DP 74.47) of FVIII. At the end of 10 days, a mean production of 4052 ng/mL of the recombinant protein in a volume of 50 mL was obtained, totaling a production of 202.6 µg FVIIr, which corresponds to approximately 405 IU. The productivity ($C_{max}/t$) in the Sk-Hep-1-FVIIr cell was 201.8 ng/mL/day.

Figure 20:
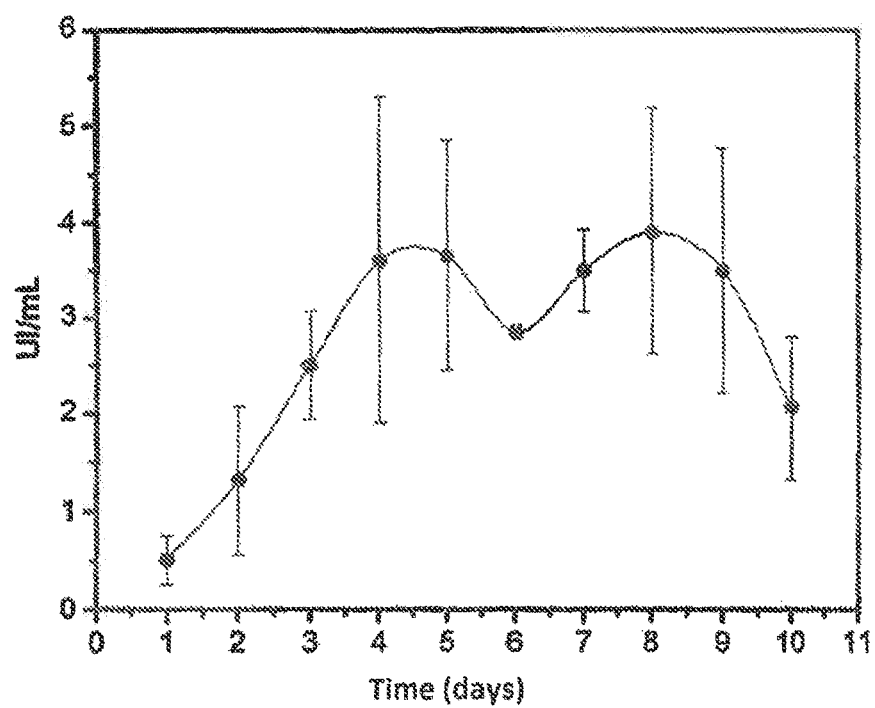
FIG. 20 graphically depicts the production kinetics of biologically active FVIIr in cultivated Sk-Hep-1-FVIIr cell line in spinner flasks for 10 days.

The kinetics of recombinant protein production were also measured in terms of the amount of biologically active FVIIr which the cells were producing. For Sk-Hep-1 cells, the kinetics of production is shown in FIG. 20. FIG. 20 shows that there was a peak of production of biologically active FVIIr on the eighth day of culture, of the order of 4 IU/ml.

When analyzing the HKB-11-FVIIr cells, these reached the maximum cell concentration, $1.61 \times 10^6$ cells/mL, on the ninth day of the experiment. The exponential growth phase occurred between on days 1 and 7 and the maximum specific growth speed (µmax) was 0.36 day$^{-1}$.

Figure 21:
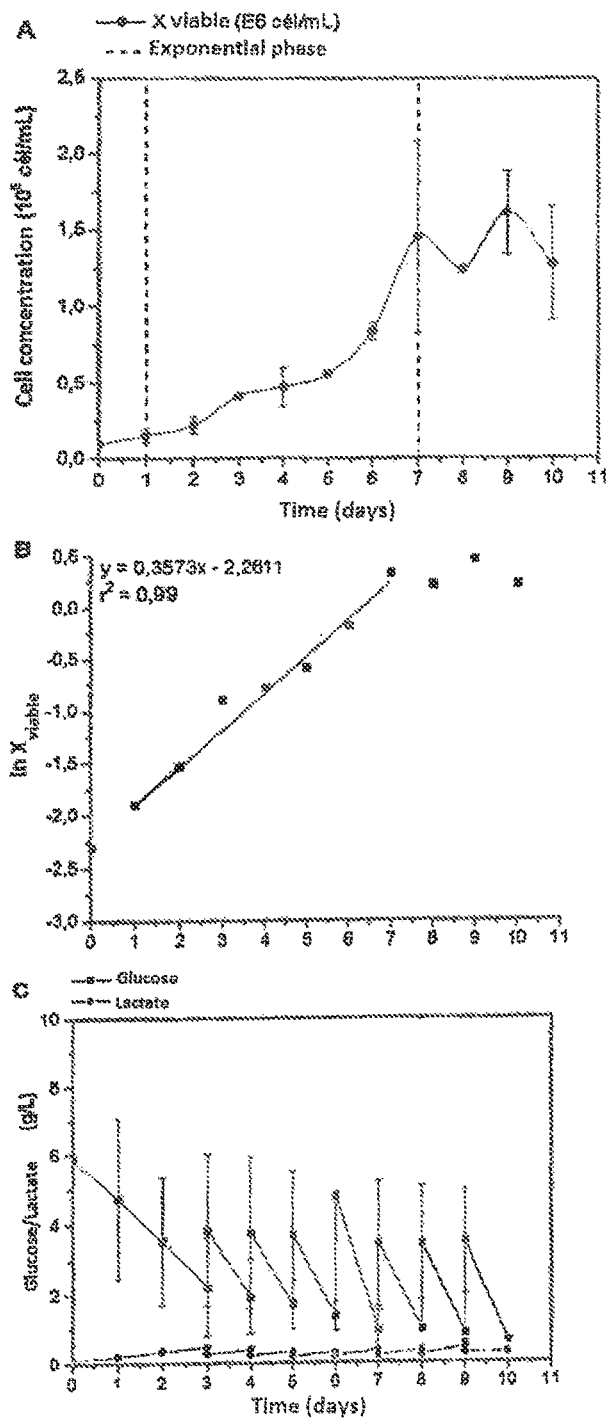
FIG. 21 graphically depicts the culture of HKB-11-FVIIr cell line in microcarriers in spinner flasks—cell growth (A), specific maximum growth speed (B) and concentration (C)

As in Sk-Hep-1 cells, over the 10 days of culture it was possible to observe a gradual consumption of glucose, as was expected, however, there was no depletion due to the 50% changes culture medium every 24 hours. Regarding the production of lactate, it was observed that it reached the maximum concentration on the ninth day of culture, with mean value of 0.47 g/L (FIG. 21).

Again, with the aim of illustrating the culture in microcarriers and expression of the GFP marker gene were made images with phase contrast microscopy and fluorescence of the cell HKB-11-FVIIr, as shown in FIG. 22.

The ELISA assay was also performed for the HKB-11 line. As shown in FIG. 23, production had its maximum peak reached on the eighth day of the experiment, reaching an average concentration of 1020 ng/mL (SD 9.8) of FVIIr. At the end of 10 days, a mean concentration of 3038 ng/mL FVIIr in 50 mL of culture medium, totaling a production of 152 µg of FVIIr, which corresponds to about 304 IU. The productivity ($C_{max}/t$) in HKB-11-FVIIr cell was 127.5 ng/mL/day.

The kinetics of recombinant protein production were also measured in terms of the amount of biologically active FVIIr which the cells were producing. For HKB-11-FVIIr cells, the kinetics of production is shown in FIG. 24. FIG. 24 shows that there was a peak of production of biologically active FVIIr on the sixth day of culture, in the order of 0.6 IU/mL.

Adaptation of Factor VII-Producing HKB-11 Cell Line to Growth in Suspension in Bovine Fetal Serum Free Medium Because of the higher productivity, the HKB-11/rFVII cell was selected for the adaptation to the growth in suspension in serum free medium (Free Style), and subsequent culture in bioreactors for production of rFVII in large scale.

As shown in FIG. 25, the rounded cell morphology, the formation of cell clusters, together with the viability greater than 85%, is indicative that the cells are in a adaptation to growth in suspension.

These results show that this cell line is an excellent candidate for rFVII production in bioreactors with bovine fetal serum free medium on industrial scale, as it presents a higher production than the commercially available BHK.

The invention claimed is:

1. A process for modifying human cell lines to produce increased levels of blood coagulation Factor VII, comprising the steps of:
   (1) providing virus particles containing a Factor FVII gene and a GFP gene as a reporter;
   (2) transducting human cell lines selected from SK-Hep 1, HKB11 and HepG 2 with the viral particles to form human Factor FVII producing cells; and
   (3) culturing the Factor human FVII producing cells from step (2) in suspension using microcarriers, wherein in the process, expression of calumenin, VKORC1 and gamma-carboxylase genes, is not altered.

2. The process according to claim 1, wherein step (1) is performed from transfecting a Hek293T cell line.

3. The process according to claim 2, wherein the transfection is performed using a lentiviral vector with transgenes and two auxiliary vectors.

4. The process according to claim 2, wherein the transfection is performed in a polyethylamine reagent and three plasmids are transfected in the following ratio: 10 to 25 µg vector with transgene p1054-rFVII; 10 to 15 µg pCMVΔR8.91; and 5 to 10 µg pMD2 VSVG.

5. The process according to claim 1, wherein in step (1) the Factor VII gene and the GFP gene are separated by an IRES element.

6. The process according to claim 2, wherein supernatant produced by the Hek293T transfected cells is placed on the culture of the cell line, in the presence of 3 to 6 µg/ml hexadimethrine bromide.

7. The process according to claim 1, wherein prior to transduction, the cells are plated in a concentration of $2\times10^5$ cells per well in a 6-well plate and viral concentration of 10 virus/cell was added, based on viral titration values.

8. The process according to claim 1, wherein in step (3) the cells are cultured in culture flasks of 75 cm² for expansion, incubated at 37° C. and 5% $CO_2$ until confluence of 80%; released with Trypsin-EDTA and inoculated in T-flasks of 75 cm², after reaching a number of $5\times10^6$ cells; and are inoculated in a spinner flask already containing culture medium and microcarrier.

9. The process according to claim 8, wherein the microcarrier is at the concentration of 3.0 g/L.

10. The process according to claim 3, wherein the transfection is performed using a polyethylamine reagent and three plasmids are transfected in the following ratio: 10 to 25 μg vector with transgene p1054-rFVII; 10 to 15 μg pCMVΔR8.91; and 5 to 10 μg pMD2 VSVG.

11. The process according to claim 2, wherein in step (1) the Factor VII gene and the GFP gene are separated by an IRES element.

12. The process according to claim 3, wherein in step (1) the Factor VII gene and the GFP gene are separated by an IRES element.

13. The process according to claim 4, wherein in step (1) the Factor VII gene and the GFP gene are separated by an IRES element.

14. The process according to claim 10, wherein in step (1) the Factor VII gene and the GFP gene are separated by an IRES element.

* * * * *